United States Patent
Cui et al.

(10) Patent No.: US 10,973,853 B2
(45) Date of Patent: Apr. 13, 2021

(54) ANTIBODIES TO T CELL IMMUNORECEPTOR WITH IG AND ITIM DOMAINS (TIGIT) AND USES THEREOF

(71) Applicant: I-Mab Biopharma US Limited, Gaithersburg, MD (US)

(72) Inventors: Feifei Cui, Shanghai (CN); Lei Fang, Shanghai (CN); Bingshi Guo, Shanghai (CN); Zhengyi Wang, Shanghai (CN); Jingwu Zang, Shanghai (CN)

(73) Assignee: I-Mab Biopharma US Limited, Gaithersburg, MD (US)

( * ) Notice: Subject to any disclaimer, the term of this patent is extended or adjusted under 35 U.S.C. 154(b) by 48 days.

(21) Appl. No.: 16/483,870

(22) PCT Filed: Feb. 11, 2019

(86) PCT No.: PCT/CN2019/074775
§ 371 (c)(1),
(2) Date: Aug. 6, 2019

(87) PCT Pub. No.: WO2019/154415
PCT Pub. Date: Aug. 15, 2019

(65) Prior Publication Data
US 2021/0015858 A1 Jan. 21, 2021

(30) Foreign Application Priority Data

Feb. 6, 2018 (WO) .............. PCT/CN2018/075477

(51) Int. Cl.
*A61K 39/00* (2006.01)
*A61K 35/17* (2015.01)
*A61P 31/18* (2006.01)
*A61P 35/00* (2006.01)
*C07K 16/28* (2006.01)

(52) U.S. Cl.
CPC .............. *A61K 35/17* (2013.01); *A61P 31/18* (2018.01); *A61P 35/00* (2018.01); *C07K 16/2809* (2013.01); *A61K 2039/505* (2013.01)

(58) Field of Classification Search
CPC .............................................. A61K 2039/505
See application file for complete search history.

(56) References Cited

U.S. PATENT DOCUMENTS

2020/0255516 A1* 8/2020 Fu ..................... C07K 16/2803

FOREIGN PATENT DOCUMENTS

| CN | 107073108 A | 8/2017 |
|---|---|---|
| CN | 107148430 A | 9/2017 |
| CN | 107207594 A | 9/2017 |
| WO | 2015009856 A2 | 1/2015 |
| WO | WO 2017/030823 | 2/2017 |
| WO | WO 2017/053748 | 3/2017 |
| WO | WO 2017037707 | 3/2017 |
| WO | WO 2017/059095 | 4/2017 |
| WO | 2019129261 A1 | 7/2019 |

OTHER PUBLICATIONS

Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Yu et al. (PLoS One. 2012; 7 (3): e33340; pp. 1-15).*
Chang et al. (Structure. Jan. 7, 2014; 22 (1): 9-21).*
Ingram et al. (Proc. Natl. Acad. Sci. USA. Apr. 10, 2018; 115 (15): 3912-3917).*
Kipps et al. (J. Exp. Med. Jan. 1, 1985; 161 (1): 1-17).*
Gura (Science. 1997; 278: 1041-1042).*
Dennis (Nature. Aug. 7, 2006; 442: 739-741).*
Saijo et al. (Cancer Sci. Oct. 2004; 95 (10): 772-776).*
Kelland (Eur. J. Cancer. Apr. 2004; 40 (6): 827-836).*
Bergers et al. (Current Opinion in Genetics and Development. 2000; 10: 120-127).*
Brodská et al. (Cancer Immunol. Res. Oct. 2016; 4 (10): 815-819).*
Winkler et al. (J. Immunol. Oct. 15, 2000; 165 (8): 4505-4514).*
Communication pursuant to Rule 164(1) EPC fer EP Application No. 19730103.9 dated Jul. 17, 2020, 9 pages.
International Search Report and Written Opinion of PCT/CN2019/074775 dated Apr. 28, 2019 and Apr. 28, 2019 (17 pages).
Extended European Search Report for EP Application No. 19730103.9 dated Dec. 8, 2020, 8 pages.

\* cited by examiner

*Primary Examiner* — Stephen L Rawlings
(74) *Attorney, Agent, or Firm* — Sheppard Mullin Richter & Hampton LLP

(57) ABSTRACT

The present disclosure provides antibodies and fragments thereof having specificity to a human T cell immunoreceptor with Ig and ITIM domains (TIGIT) protein. Methods of using the antibodies or fragments thereof for treating and diagnosing diseases such as cancer and viral infections are also provided.

7 Claims, 13 Drawing Sheets
Specification includes a Sequence Listing.

ANTIBODIES TO T CELL IMMUNORECEPTOR WITH IG AND ITIM DOMAINS (TIGIT) AND USES THEREOF

CROSS REFERENCE TO RELATED APPLICATIONS

The present application is the U.S. national stage application of International Application PCT/CN2019/074775, filed Feb. 11, 2019, which claims priority to International Application PCT/CN2018/075477, filed Feb. 6, 2018, the contents of each of which are incorporated herein by reference in their entireties in the present disclosure.

BACKGROUND

TIGIT (also called T cell immunoreceptor with Ig and ITIM domains) is an immune receptor expressed on certain T cells and Natural Killer (NK) cells. Research has shown that TIGIT-Fc fusion protein could interact with PVR on dendritic cells and increase its IL-10 secretion level and decrease its IL-12 secretion level under LPS stimulation, and also inhibit T cell activation in vivo. TIGIT's inhibition of NK cytotoxicity can be blocked by antibodies against its interaction with PVR and the activity is directed through its ITIM domain.

TIGIT is expressed by activated cytotoxic T cells and regulatory T cells and has also been shown to be unregulated on T cells in multiple cancer models. The ligands CD155 and CD112 are found on dendritic cells and macrophages and are also highly expressed in several types of cancer. Additionally, TIGIT expression is highly correlated with the expression of other coinhibitory molecules, including PD-1. Overall, this suggests that tumors upregulate the TIGIT pathway along with other inhibitory checkpoint networks to promote immunosuppressive mechanisms.

Further, during Human Immunodeficiency Virus (HIV) infection, TIGIT expressing CD8+ T cells has been shown to be expanded and associated with clinical markers of HIV disease progression in a diverse group of HIV infected individuals. Elevated TIGIT levels remained sustained even among those with undetectable viral loads and a large fraction of HIV-specific CD8+ T cells simultaneously express both TIGIT and another negative checkpoint receptor, Programmed Death Protein 1 (PD-1) and retained several features of exhausted T cells. Blocking these pathways with targeted monoclonal antibodies synergistically rejuvenated HIV-specific CD8+ T cell responses. This pathway can potentially be targeted to enhance killing of HIV infected cells during "Shock and Kill" HIV curative approaches.

SUMMARY

The present disclosure provides antibodies and fragments thereof having specificity to a human T cell immunoreceptor with Ig and ITIM domains (TIGIT) protein. The experimental data demonstrate that these antibodies exhibited high affinity to TIGIT and are functionally active. Methods of using the antibodies or fragments thereof for treating and diagnosing diseases such as cancer and viral infections are also provided.

One embodiment of the present disclosure provides an isolated antibody or fragment thereof having specificity to a human T cell immunoreceptor with Ig and ITIM domains (TIGIT) protein, wherein the antibody or fragment thereof comprises a heavy chain variable region comprising heavy chain complementarity determining regions HCDR1, HCDR2, and HCDR3, and a light chain variable region comprising light chain complementarity determining regions LCDR1, LCDR2, and LCDR3, wherein the HCDR1, HCDR2, HCDR3, LCDR1, LCDR2, and LCDR3 are selected from the group consisting of:

(a) HCDR1:
(SEQ ID NO: 29)
ENTMH,

HCDR2:
(SEQ ID NO: 30)
GINPNQGGNRNNQKFKG,

HCDR3:
(SEQ ID NO: 31)
SGLRDYAMDY,

LCDR1:
(SEQ ID NO: 32)
KASQHVSTAVV,

LCDR2:
(SEQ ID NO: 33)
SPSYRYT,
and

LCDR3:
(SEQ ID NO: 34)
QQHYSTPWT;

(b) HCDR1:
(SEQ ID NO: 43)
DYYMY,

HCDR2:
(SEQ ID NO: 44)
SITKGGGSTYYPDTLKG,

HCDR3:
(SEQ ID NO: 45)
QSSYDFVMDY,

LCDR1:
(SEQ ID NO: 46)
KASQDVDTAVA,

LCDR2:
(SEQ ID NO: 47)
WASARHT,
and

LCDR3:
(SEQ ID NO: 48)
QQYSNYPLT;
and (c) HCDR1:
(SEQ ID NO: 57)
SDYAWN,

HCDR2:
(SEQ ID NO: 58)
YISYSGNTRYNPSLKS,

HCDR3:
(SEQ ID NO: 59)
KYYGSWFPY,

LCDR1:
(SEQ ID NO: 60)
KASQDVFTAVA,

LCDR2:
(SEQ ID NO: 61)
SASYRYT,
and

-continued

LCDR3:
(SEQ ID NO: 62)
QQHYSTPWT.

In some embodiments, the antibody or fragment further comprises a heavy chain constant region, a light chain constant region, an Fc region, or the combination thereof. In some embodiments, the antibody or fragment thereof is of an isotype of IgG, IgM, IgA, IgE or IgD. In some embodiments, the antibody is a chimeric antibody, a humanized antibody, or a fully human antibody.

In some embodiments, the HCDR1, HCDR2, HCDR3, LCDR1, LCDR2, and LCDR3 are HCDR1: ENTMH (SEQ ID NO: 29), HCDR2: GINPNQGGNRNNQKFKG (SEQ ID NO: 30), HCDR3: SGLRDYAMDY (SEQ ID NO: 31), LCDR1: KASQHVSTAVV (SEQ ID NO: 32), LCDR2: SPSYRYT (SEQ ID NO: 33), and LCDR3: QQHYSTPWT (SEQ ID NO: 34).

Such an antibody or fragment can be humanized and the heavy chain variable region comprises one or more back mutations selected from the group consisting of 12V, 20L, 24T, 38K, 48I, 68A, 70L, 72V and 91S, according to Kabat numbering, and combinations thereof. In some embodiments, the light chain variable region comprises one or more back mutations selected from the group consisting of 13T, 73F, 78V and 104L, according to Kabat numbering, and combinations thereof. In some embodiments, In some embodiments, the antibody or fragment comprises a heavy chain variable region comprising an amino acid sequence selected from the group consisting of SEQ ID NO: 1, and 35-38, or a peptide having at least 90% sequence identity to an amino acid sequence selected from the group consisting of SEQ ID NO: 1, and 35-38. In some embodiments, the antibody or fragment comprises a light chain variable region comprising an amino acid sequence selected from the group consisting of SEQ ID NO: 2, and 39-42, or a peptide having at least 90% sequence identity to an amino acid sequence selected from the group consisting of SEQ ID NO: 2, and 39-42.

In some embodiments, the HCDR1, HCDR2, HCDR3, LCDR1, LCDR2, and LCDR3 are HCDR1: DYYMY (SEQ ID NO: 43), HCDR2: SITKGGGSTYYPDTLKG (SEQ ID NO: 44), HCDR3: QSSYDFVMDY (SEQ ID NO: 45), LCDR1: KASQDVDTAVA (SEQ ID NO: 46), LCDR2: WASARHT (SEQ ID NO: 47), and LCDR3: QQYSNYPLT (SEQ ID NO: 48).

Such an antibody or fragment can be humanized and the heavy chain variable region comprises one or more back mutations selected from the group consisting of 3K, 44R, and 82R, according to Kabat numbering, and combinations thereof. In some embodiments, the light chain variable region comprises one or more back mutations selected from the group consisting of 3V, 42Q, 43S, and 87F, according to Kabat numbering, and combinations thereof.

In some embodiments, the antibody or fragment comprises a heavy chain variable region comprising an amino acid sequence selected from the group consisting of SEQ ID NO: 27, and 49-52, or a peptide having at least 90% sequence identity to an amino acid sequence selected from the group consisting of SEQ ID NO: 27, and 49-52. In some embodiments, the antibody or fragment comprises a light chain variable region comprising an amino acid sequence selected from the group consisting of SEQ ID NO: 28, and 53-56, or a peptide having at least 90% sequence identity to an amino acid sequence selected from the group consisting of SEQ ID NO: 28, and 53-56.

In some embodiments, the HCDR1, HCDR2, HCDR3, LCDR1, LCDR2, and LCDR3 are HCDR1: SDYAWN (SEQ ID NO: 57), HCDR2: YISYSGNTRYNPSLKS (SEQ ID NO: 58), HCDR3: KYYGSWFPY (SEQ ID NO: 59), LCDR1: KASQDVFTAVA (SEQ ID NO: 60), LCDR2: SASYRYT (SEQ ID NO: 61), and LCDR3: QQHYSTPWT (SEQ ID NO: 62).

Such an antibody or fragment can be humanized and the heavy chain variable region comprises one or more back mutations selected from the group consisting of 49M, 68I, 72R, 83F and 97S, according to Kabat numbering, and combinations thereof. In some embodiments, the light chain variable region comprises one or more back mutations selected from the group consisting of 13T, 73F and 78V, according to Kabat numbering, and combinations thereof.

In some embodiments, the antibody or fragment comprises a heavy chain variable region comprising an amino acid sequence selected from the group consisting of SEQ ID NO: 3, and 63-66, or a peptide having at least 90% sequence identity to an amino acid sequence selected from the group consisting of SEQ ID NO: 3, and 63-66.

In some embodiments, the antibody or fragment comprises a light chain variable region comprising an amino acid sequence selected from the group consisting of SEQ ID NO: 4, and 67-70, or a peptide having at least 90% sequence identity to an amino acid sequence selected from the group consisting of SEQ ID NO: 4, and 67-70.

Also provided, in one embodiment, is an isolated antibody or fragment thereof having specificity to a human T cell immunoreceptor with Ig and ITIM domains (TIGIT) protein, wherein the antibody or fragment thereof comprises a heavy chain variable region comprising heavy chain complementarity determining regions HCDR1, HCDR2, and HCDR3, and a light chain variable region comprising light chain complementarity determining regions LCDR1, LCDR2, and LCDR3, wherein the HCDR1, HCDR2, HCDR3, LCDR1, LCDR2, and LCDR3 are selected from the group consisting of:

(a) HCDR1:
(SEQ ID NO: 29)
ENTMH,

HCDR2:
(SEQ ID NO: 30)
GINPNQGGNRNNQKFKG,

HCDR3:
(SEQ ID NO: 31)
SGLRDYAMDY,

LCDR1:
(SEQ ID NO: 32)
KASQHVSTAVV,

LCDR2:
(SEQ ID NO: 33)
SPSYRYT,
and

LCDR3:
(SEQ ID NO: 34)
QQHYSTPWT;

(b) HCDR1:
(SEQ ID NO: 43)
DYYMY,

HCDR2:
(SEQ ID NO: 44)
SITKGGGSTYYPDTLKG,

```
HCDR3:
                                           (SEQ ID NO: 45)
QSSYDFVMDY,

LCDR1:
                                           (SEQ ID NO: 46)
KASQDVDTAVA,

LCDR2:
                                           (SEQ ID NO: 47)
WASARHT,
and

LCDR3:
                                           (SEQ ID NO: 48)
QQYSNYPLT;

(c) HCDR1:
                                           (SEQ ID NO: 57)
SDYAWN,

HCDR2:
                                           (SEQ ID NO: 58)
YISYSGNTRYNPSLKS,

HCDR3:
                                           (SEQ ID NO: 59)
KYYGSWFPY,

LCDR1:
                                           (SEQ ID NO: 60)
KASQDVFTAVA,

LCDR2:
                                           (SEQ ID NO: 61)
SASYRYT,
and

LCDR3:
                                           (SEQ ID NO: 62)
QQHYSTPWT;
and (d) HCDR1, HCDR2, HCDR3, LCDR1, LCDR2, and LCDR3 ,
``` as shown in (a)-(c) but at least one of which includes one, two, or three amino acid addition, deletion, conservative amino acid substitution or the combinations thereof.

In some embodiments, the HCDR1, HCDR2, HCDR3, LCDR1, LCDR2, and LCDR3 are HCDR1: SDYAWN (SEQ ID NO: 57), HCDR2: YISYSGNTRYNPSLKS (SEQ ID NO: 58), HCDR3: KYYGSWFPY (SEQ ID NO: 59), LCDR1: KASQDVFTAVA (SEQ ID NO: 60), LCDR2: SASYRYT (SEQ ID NO: 61), and LCDR3: QQHYSTPWT (SEQ ID NO: 62), or SEQ ID NO: 57-62, at least one of which includes one, two, or three amino acid substitution.

In some embodiments, the amino acid substitution is at one or residues selected from the group consisting of VH-31S, VH-57N, VH-59R, VH-66S, VH-100Y, VH-103S, VH-107Y, VL-53Y, VL-55Y, VL-56T, and VL-91H, according to Kabat numbering, and combinations thereof. In some embodiments, the substitution is one or more selected from Table 13.

Also provided are antibodies or fragments thereof having HCDR1, HCDR2, and HCDR3 with the amino acid sequences of the HCDR1, HCDR2, and HCDR3 of a heavy chain variable region selected from the group consisting of SEQ ID NO:3 and 71-75, respectively, and LCDR1, LCDR2, and LCDR3 with the amino acid sequences of the LCDR1, LCDR2, and LCDR3 of a light chain variable region selected from the group consisting of SEQ ID NO: 4 and 76-80, respectively.

In some embodiments, the antibody or fragment is bispecific. The bispecificity may include a second specificity to an immune checkpoint protein or a tumor antigen. In some embodiments, the second specificity is to a protein target selected from the group consisting of PD-L1, PD-1, LAG3, CD47, CD73, EGFR, Her2, CD33, CD133, CEA and VEGF. In some embodiments, the second specificity to is PD-L1.

Compositions are also provided, in some embodiments, which can include the antibody or fragment of the present disclosure and a pharmaceutically acceptable carrier. Also provided is an isolated cell comprising one or more polynucleotide encoding the antibody or fragment of the present disclosure.

Methods are also provided. In one embodiment, a method of treating cancer in a patient in need thereof is provided, comprising administering to the patient the antibody or fragment thereof of the present disclosure. In some embodiments, the cancer is selected from the group consisting of bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

In another embodiment, provided is a method of treating or inhibiting infection in a patient in need thereof, comprising administering to the patient the antibody or fragment thereof of the present disclosure. In some embodiments, the infection is viral, bacterial, fungal, or parasite infection. In some embodiments, the infection is HIV infection.

Still further, one embodiment provides a method of treating cancer in a patient in need thereof, comprising: (a) treating a T cell, in vitro, with the antibody or fragment thereof of any one of claims 1-27; and (b) administering the treated T cell to the patient. In some embodiments, the method further comprises, prior to step (a), isolating the T cell from an individual. In some embodiments, the T cell is a tumor-infiltrating T lymphocyte, a CD4+ T cell, a CD8+ T cell, or the combination thereof.

Also provided, in one embodiment, is a method of detecting expression of TIGIT in a sample, comprising contacting the sample with the antibody or fragment thereof of the present disclosure under conditions for the antibody or fragment thereof to bind to the TIGIT, and detecting the binding which indicates expression of TIGIT in the sample.

Still further provided, in one embodiment, is a method of identifying a patient suitable for treatment with an anti-TIGIT therapy, comprising isolated a cell from the cancer patient and detecting the presence of a TIGIT protein with the antibody or fragment thereof of the present disclosure.

DETAILED DESCRIPTION

Definitions

Figure 1:
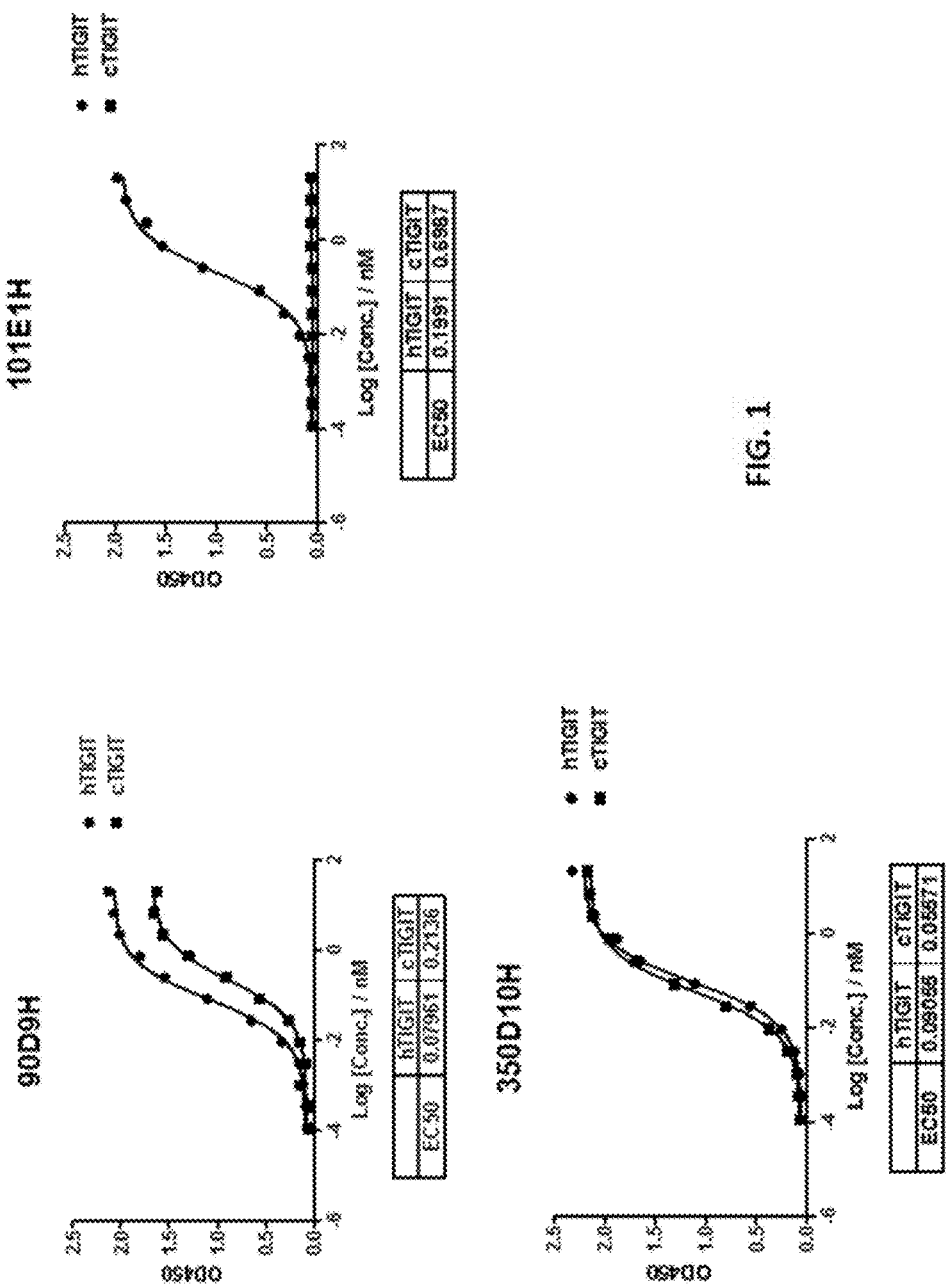
FIG. 1 shows the $EC_{50}$ for binding to human and cyno TIGIT protein for antibodies 90D9H, 101E1H and 350D10H.
Figure 2:
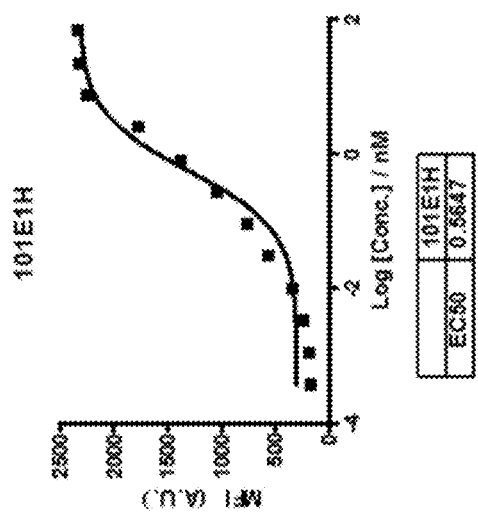
FIG. 2 shows that the 90D9H, 101E1H, and 350D10H antibodies dose-dependently bound to TIGIT expressed on Jurkat cell line.
Figure 2:
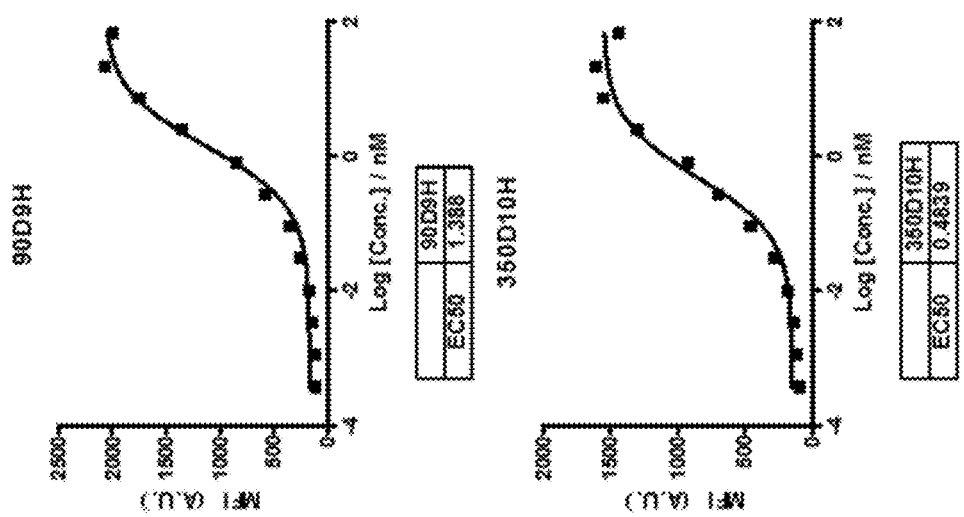

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and $F(ab')_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (K, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, *J. Mol. Biol.*, 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

|  | Kabat | Chothia |
| --- | --- | --- |
| CDR-H1 | 31-35 | 26-32 |
| CDR-H2 | 50-65 | 52-58 |
| CDR-H3 | 95-102 | 95-102 |
| CDR-L1 | 24-34 | 26-32 |
| CDR-L2 | 50-56 | 50-52 |
| CDR-L3 | 89-97 | 91-96 |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-TIGIT Antibodies

The present disclosure provides anti-TIGIT antibodies with high affinity and inhibitory activity on the human TIGIT protein. The antibodies can bind effectively to both free TIGIT and TIGIT on surfaces of cells such as Jurkat cells and activated CD8+ T cells. Further, they can effectively inhibit the binding of TIGIT to the receptor CD155, whether in a solution or when the TIGIT is express on cell surface. Such binding and inhibition, moreover, result in enhanced jurkat cell-mediated IL-2 production and inhibition of tumor growth.

In accordance with one embodiment of the present disclosure, provided is an antibody that includes the heavy chain and light chain variable domains with the CDR regions as shown in VH-VL pairs:

| VH-VL Pair No. | VH | SEQ ID NO: | VL | SEQ ID NO: |
|---|---|---|---|---|
| 1 | 90D9-VH | 1 | 90D9-VL | 2 |
| 2 | 101E1-VH | 3 | 101E1-VL | 4 |
| 3 | 116H8-VH | 5 | 116H8-VL | 6 |
| 4 | 118A12-VH | 7 | 118A12-VL | 8 |
| 5 | 131A12-VH | 9 | 131A12-VL | 10 |
| 6 | 143B6-VH | 11 | 143B6-VL | 12 |
| 7 | 167F7-VH | 13 | 167F7-VL | 14 |
| 8 | 221F11-VH | 15 | 221F11-VL | 16 |
| 9 | 222H4-VH | 17 | 222H4-VL | 18 |
| 10 | 327C9-VH | 19 | 327C9-VL | 20 |
| 11 | 342A9-VH | 21 | 342A9-VL | 22 |
| 12 | 344F2-VH | 23 | 344F2-VL | 24 |
| 13 | 349H6-VH | 25 | 349H6-VL | 26 |
| 14 | 350D10-VH | 27 | 350D10-VL | 28 |

In particular, the CDR regions can be those from 90D9-VH (CDRs in SEQ ID NO: 29-31) and 90D9-VL (CDRs in SEQ ID NO: 32-34), 101E1-VH (CDRs in SEQ ID NO: 57-59) and 101E1-VL (CDRs in SEQ ID NO: 60-62), or 350D10-VH (CDRs in SEQ ID NO: 43-45) and 350D10-VL (CDRs in SEQ ID NO: 46-48).

These antibodies may be mouse antibodies, chimeric antibodies, humanized antibody or human antibodies, without limitation. During humanizations, certain back-mutations were identified to be helpful to ensure the binding affinity of the antibodies. Such back-mutations, in some embodiments, for those having the CDRs of 90D9, include 12V (i.e., residue at location 12 of the humanized antibody is mutated back to Val), 20L, 24T, 38K, 48I, 68A, 70L, 72V and 91S in the heavy chain and 13T, 73F, 78V and 104L in the light chain, all according to Kabat numbering.

For antibodies or fragments having the CDRs of 350D10, the back-mutations can be one or more of 3K, 44R, and 82R in the heavy chain and 3V, 42Q, 43S, and 87F in the light chain, all according to Kabat numbering.

For antibodies or fragments having the CDRs of 101E1, the back-mutations can be one or more of 49M, 68I, 72R, 83F and 97S in the heavy chain and 13T, 73F and 78V in the light chain, all according to Kabat numbering.

As demonstrated in the experimental examples, the antibodies that contained these CDR regions, whether mouse, humanized or chimeric, had potent TIGIT binding and inhibitory activities. Further experiments indicated that certain residues within the CDR can be modified to retain or improve the property of the antibodies. Such residues are referred to as "hot spots" which are underlined in the tables below. In some embodiments, an anti-TIGIT antibody of the present disclosure includes the VH and VL CDR as listed below, with one, two or three further modifications. Such modifications can be addition, deletion or substitution of amino acids. In some embodiments, no more than one, or two, or three CDR an amino acid substitution. Some example substitutions are shown below for antibodies with CDRs derived from 101E1.

Residues (underlined) in the CDRs of 101E1 that can be substituted to improve binding

| Name | Sequences (SEQ ID NO:) | Kabat Numbering |
|---|---|---|
| VH CDR1 | SDYAWN (57) | S31 |
| VH CDR2 | YISYSGNTRYNPSLKS (58) | N57, R59, S66 |
| VH CDR3 | KYYGSWFPY (59) | Y100, S103, Y107 |
| VL CDR1 | KASQDVFTAVA (60) | |
| VL CDR2 | SASYRYT (61) | Y53, Y55, T56 |
| VL CDR3 | QQHYSTPWT (62) | H91 |

Example suitable substitutions at these residues

| Residue | Substituted with |
|---|---|
| VH-S31 | Q, R, or D |
| VH-N57 | E, H, A, T, S, V, M, Q, D, or I |
| VH-R59 | L, M, P, K, or S |
| VH-S66 | N, D, or G |
| VH-Y100 | D, or H |
| VH-S103 | G |
| VH-Y107 | I, V, N, L, S, D, E, R, or Q |
| VL-Y53 | N, or H |
| VL-Y55 | H, E, C, D, T, K, A, N, Q, P, N, or M |
| VL-T56 | N |
| VL-H91 | N, P, E, L, S, T, C, R, I, K, F, G, Y, H, or A |

In some embodiments, the modification is substitution at no more than one hot spot position from each of the CDRs. In some embodiments, the modification is substitution at one, two or three such hot spot positions. In one embodiment, the modification is substitution at one of the hot spot positions. Such substitutions, in some embodiments, are conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

Amino Acid Similarity Matrix

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", *Immunol. Rev.* (52:119-58 (1982)).

Bi-Functional Molecules

TIGIT is an immune receptor present on some T cells and NK cells. As an immune receptor targeting molecule, an antibody or antigen-binding fragment specific to TIGIT can be combined with a second antigen-binding fragment specific to a tumor cell or an immune checkpoint to generate a bispecific antibody.

In some embodiments, the immune cell is selected from the group consisting of a T cell, a B cell, a monocyte, a macrophage, a neutrophil, a dendritic cell, a phagocyte, a natural killer cell, an eosinophil, a basophil, and a mast cell. Molecules on the immune cell which can be targeted include, for example, CD3, CD16, CD19, CD28, and CD64. Other examples include PD-1, PD-L1, CTLA-4, LAG-3 (also known as CD223), CD28, CD122, 4-1BB (also known as CD137), TIM3, OX-40 or OX40L, CD40 or CD40L, LIGHT, ICOS/ICOSL, GITR/GITRL, TIGIT, CD27, VISTA, B7H3, B7H4, HEVM or BTLA (also known as CD272), killer-cell immunoglobulin-like receptors (KIRs), and CD47. Specific examples of bispecificity include, without limitation, TIGIT/PD-L1, TIGIT/PD-1, TIGIT/LAG3, and TIGIT/CD47.

As an immune receptor inhibitor, an antibody or antigen-binding fragment specific to TIGIT can be combined with a second antigen-binding fragment specific to a tumor antigen to generate a bispecific antibody. A "tumor antigen" is an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

An abundance of tumor antigens are known in the art and new tumor antigens can be readily identified by screening. Non-limiting examples of tumor antigens include EGFR, Her2, EpCAM, CD20, CD30, CD33, CD47, CD52, CD133, CD73, CEA, gpA33, Mucins, TAG-72, CIX, PSMA, folate-binding protein, GD2, GD3, GM2, VEGF, VEGFR, Integrin, αVβ3, α5β1, ERBB2, ERBB3, MET, IGF1R, EPHA3, TRAILR1, TRAILR2, RANKL, FAP and Tenascin.

In some aspects, the monovalent unit has specificity to a protein that is overexpressed on a tumor cell as compared to a corresponding non-tumor cell. A "corresponding non-tumor cell" as used here, refers to a non-tumor cell that is of the same cell type as the origin of the tumor cell. It is noted that such proteins are not necessarily different from tumor antigens. Non-limiting examples include carcinoembryonic antigen (CEA), which is overexpressed in most colon, rectum, breast, lung, pancreas and gastrointestinal tract carcinomas; heregulin receptors (HER-2, neu or c-erbB-2), which is frequently overexpressed in breast, ovarian, colon, lung, prostate and cervical cancers; epidermal growth factor receptor (EGFR), which is highly expressed in a range of solid tumors including those of the breast, head and neck, non-small cell lung and prostate; asialoglycoprotein receptor; transferrin receptor; serpin enzyme complex receptor, which is expressed on hepatocytes; fibroblast growth factor receptor (FGFR), which is overexpressed on pancreatic ductal adenocarcinoma cells; vascular endothelial growth factor receptor (VEGFR), for anti-angiogenesis gene therapy; folate receptor, which is selectively overexpressed in 90% of nonmucinous ovarian carcinomas; cell surface glycocalyx; carbohydrate receptors; and polymeric immunoglobulin receptor, which is useful for gene delivery to respiratory epithelial cells and attractive for treatment of lung diseases such as Cystic Fibrosis. Non-limiting examples of bispecificity in this respect include TIGIT/EGFR, TIGIT/Her2, TIGIT/CD33, TIGIT/CD133, TIGIT/CEA and TIGIT/VEGF.

Different format of bispecific antibodies are also provided. In some embodiments, each of the anti-TIGIT fragment and the second fragment each is independently selected from a Fab fragment, a single-chain variable fragment (scFv), or a single-domain antibody. In some embodiments, the bispecific antibody further includes a Fc fragment.

Bifunctional molecules that include not just antibody or antigen binding fragment are also provided. As a tumor antigen targeting molecule, an antibody or antigen-binding fragment specific to TIGIT, such as those described here, can be combined with an immune cytokine or ligand optionally through a peptide linker. The linked immune cytokines or ligands include, but not limited to, IL-2, IL-3, IL-4, IL-5, IL-6, IL-7, IL-10, IL-12, IL-13, IL-15, GM-CSF, TNF-α, CD40L, OX40L, CD27L, CD30L, 4-1BBL, LIGHT and GITRL. Such bi-functional molecules can combine the immune checkpoint blocking effect with tumor site local immune modulation.

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Treatment Methods

As described herein, the antibodies, variants or derivatives of the present disclosure may be used in certain treatment and diagnostic methods.

The present disclosure is further directed to antibody-based therapies which involve administering the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

In some embodiments, provided are methods for treating a cancer in a patient in need thereof. The method, in one embodiment, entails administering to the patient an effective amount of an antibody of the present disclosure. In some embodiments, at least one of the cancer cells (e.g., stromal cells) in the patient over-express TIGIT.

Non-limiting examples of cancers include bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

Cellular therapies, and more specifically chimeric antigen receptor (CAR) T-cell therapies, are also provided in the present disclosure. A suitable T cell can be used, that is put in contact with an anti-TIGIT antibody of the present disclosure (or alternatively engineered to express an anti-TIGIT antibody of the present disclosure). Upon such contact or engineering, the T cell can then be introduced to a cancer patient in need of a treatment. The cancer patient may have a cancer of any of the types as disclosed herein. The T cell can be, for instance, a tumor-infiltrating T lymphocyte, a CD4+ T cell, a CD8+ T cell, or the combination thereof, without limitation.

In some embodiments, the T cell was isolated from the cancer patient him- or her-self. In some embodiments, the T cell was provided by a donor or from a cell bank. When the T cell is isolated from the cancer patient, undesired immune reactions can be minimized.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracistemally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrastemal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

In a further embodiment, the compositions of the disclosure are administered in combination with an antineoplastic agent, an antiviral agent, antibacterial or antibiotic agent or antifungal agents. Any of these agents known in the art may be administered in the compositions of the current disclosure.

In another embodiment, compositions of the disclosure are administered in combination with a chemotherapeutic agent. Chemotherapeutic agents that may be administered with the compositions of the disclosure include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the disclosure are administered in combination with cytokines. Cytokines that may be administered with the compositions of the disclosure include, but are not limited to, IL-2, IL-3, IL-4, IL-5, IL-6, IL-7, IL-10, IL-12, IL-13, IL-15, anti-CD40, CD40L, and TNF-α.

In additional embodiments, the compositions of the disclosure are administered in combination with other therapeutic or prophylactic regimens, such as, for example, radiation therapy.

The anti-TIGIT antibodies of the present disclosure can be used, in some embodiments, together with an immune checkpoint inhibitor. Immune checkpoints are molecules in the immune system that either turn up a signal (co-stimulatory molecules) or turn down a signal. Many cancers protect themselves from the immune system by inhibiting the T cell signal. An immune checkpoint inhibitor can help stop such a protective mechanism by the cell cells. An immune checkpoint inhibitor may target any one or more of the following checkpoint molecules, PD-1, PD-L1, CTLA-4, LAG-3 (also known as CD223), CD28, CD122, 4-1BB (also known as CD137), or BTLA (also known as CD272).

Programmed T cell death 1 (PD-1) is a trans-membrane protein found on the surface of T cells, which, when bound to programmed T cell death ligand 1 (PD-L1) on tumor cells, results in suppression of T cell activity and reduction of T cell-mediated cytotoxicity. Thus, PD-1 and PD-L1 are immune down-regulators or immune checkpoint "off switches". Example PD-1 inhibitor include, without limitation, nivolumab, (Opdivo) (BMS-936558), pembrolizumab (Keytruda), pidilizumab, AMP-224, MEDI0680 (AMP-514), PDR001, MPDL3280A, MEDI4736, BMS-936559 and MSB0010718C.

Programmed death-ligand 1 (PD-L1) also known as cluster of differentiation 274 (CD274) or B7 homolog 1 (B7-H1) is a protein that in humans is encoded by the CD274 gene. Non-limiting examples of PD-L1 inhibitor include Atezolizumab (Tecentriq), Durvalumab (MEDI4736), Avelumab (MSB0010718C), MPDL3280A, BMS935559 (MDX-1105) and AMP-224.

CTLA-4 is a protein receptor that downregulates the immune system. Non-limiting examples of CTLA-4 inhibitors include ipilimumab (Yervoy) (also known as BMS-734016, MDX-010, MDX-101) and tremelimumab (formerly ticilimumab, CP-675,206).

Lymphocyte-activation gene 3 (LAG-3) is an immune checkpoint receptor on the cell surface works to suppress an immune response by action to Tregs as well as direct effects on CD8+ T cells. LAG-3 inhibitors include, without limitation, LAG525 and BMS-986016.

CD28 is constitutively expressed on almost all human CD4+ T cells and on around half of all CD8 T cells. prompts T cell expansion. Non-limiting examples of CD28 inhibitors include TGN1412.

CD122 increases the proliferation of CD8+ effector T cells. Non-limiting examples include NKTR-214.

4-1BB (also known as CD137) is involved in T-cell proliferation. CD137-mediated signaling is also known to protect T cells, and in particular, CD8+ T cells from activation-induced cell death. PF-05082566, Urelumab (BMS-663513) and lipocalin are example CD137 inhibitors.

For any of the above combination treatments, the anti-TIGIT antibody can be administered concurrently or separately from the other anticancer agent. When administered separately, the anti-TIGIT antibody can be administered before or after the other anticancer agent.

In one embodiment, a method of treating or inhibiting infection in a patient in need thereof is provided, comprising administering to the patient an effective amount of the antibody or fragment thereof of the present disclosure. In some embodiments, the infection is viral infection, bacterial infection, fungal infection or infection by a parasite.

Infection is the invasion of an organism's body tissues by disease-causing agents, their multiplication, and the reaction of host tissues to these organisms and the toxins they produce. An infection can be caused by infectious agents such as viruses, viroids, prions, bacteria, nematodes such as parasitic roundworms and pinworms, arthropods such as ticks, mites, fleas, and lice, fungi such as ringworm, and other macroparasites such as tapeworms and other helminths. In one aspect, the infectious agent is a bacterium, such as Gram negative bacterium. In one aspect, the infectious agent is virus, such as DNA viruses, RNA viruses, and reverse transcribing viruses. Non-limiting examples of viruses include Adenovirus, Coxsackievirus, Epstein-Barr virus, Hepatitis A virus, Hepatitis B virus, Hepatitis C virus, Herpes simplex virus, type 1, Herpes simplex virus, type 2, Cytomegalovirus, Human herpesvirus, type 8, HIV, Influenza virus, Measles virus, Mumps virus, Human papillomavirus, Parainfluenza virus, Poliovirus, Rabies virus, Respiratory syncytial virus, Rubella virus, Varicella-zoster virus.

The antibodies of the present disclosure can also be used to treat an infectious disease caused by a microorganism, or kill a microorganism, by targeting the microorganism and an immune cell to effect elimination of the microorganism. In one aspect, the microorganism is a virus including RNA and DNA viruses, a Gram positive bacterium, a Gram negative bacterium, a protozoa or a fungus.

Diagnostic Methods

Over-expression of TIGIT is observed in certain tumor samples, and patients having TIGIT-over-expressing cells are likely responsive to treatments with the anti-TIGIT antibodies of the present disclosure. Accordingly, the antibodies of the present disclosure can also be used for diagnostic and prognostic purposes.

A sample that preferably includes a cell can be obtained from a patient, which can be a cancer patient or a patient desiring diagnosis. The cell be a cell of a tumor tissue or a tumor block, a blood sample, a urine sample or any sample from the patient. Upon optional pre-treatment of the sample, the sample can be incubated with an antibody of the present disclosure under conditions allowing the antibody to interact with a TIGIT protein potentially present in the sample. Methods such as ELISA can be used, taking advantage of the anti-TIGIT antibody, to detect the presence of the TIGIT protein in the sample.

Presence of the TIGIT protein in the sample (optionally with the amount or concentration) can be used for diagnosis of cancer, as an indication that the patient is suitable for a treatment with the antibody, or as an indication that the patient has (or has not) responded to a cancer treatment. For a prognostic method, the detection can be done at once, twice or more, at certain stages, upon initiation of a cancer treatment to indicate the progress of the treatment.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1

Generation of Mouse Monoclonal Antibodies Against Human TIGIT

This example shows generation of anti-human-TIGIT mouse monoclonal antibodies using the hybridoma technology.

Immunizations

Recombinant human TIGIT fusion proteins containing the entire extracellular region of human TIGIT fused to a human immunoglobulin Fc domain were used as the immunogen to raise anti-human TIGIT antibodies. C57BL/6, Balb/c or SJL mice were first immunized subcutaneously (s.c.). with 50 µg immunogen and then immunized intraperitoneally (i.p.). or s.c. biweekly with 25 µg immunogen. Immune response was monitored by retroorbital bleeds. Plasma was screened by ELISA binding assay. In short, His-tagged TIGIT was coated at 0.5 µg/ml overnight and then blocked by 5% BSA in PBS. Serial diluted sera were incubated with the coated antigen for 1 h at room temperature. The resulting plates were washed with PBS/T and incubated with goat anti-mouse IgG-HRP for 1 h at room temperature. The plates were developed with TMB substrate and analyzed by spectrophotometer at OD 450-630 nm. The mice with high titers of anti-TIGIT immunoglobulin were selected for fusion and further screening. Four days prior to sacrifice and removal of the spleens, the mice were boosted i.p. with 25 µg antigen. The spleens were used for fusion.

Fusion and Hybridoma Screening

Splenocytes were electro-fused with mouse melanoma cell line SP2/0 cells and plated into 96-well culture plate. The hybridoma supernatants were tested for human TIGIT binding. Supernatants of positive clones were screened for function in blocking hTIGIT binding to its ligand hCD155 by ELISA-based receptor blocking assay. Briefly, human TIGIT huIgG Fc protein (0.3 µg/mL) was coated in 96-well plate overnight. Supernatants were diluted with PBS and incubated with coated TIGIT-huFc for 1 h at room temperature. Biotinylated-hCD155-ECD-hFc protein (0.3 µg/mL) was incubated with antibody-antigen complex for 1 hour at room temperature. Streptavidin-HRP was used to detect biotinylated-hCD155 when it bound to coated TIGIT. Clones showing strong blocking ability in this assay were selected for subcloning. Supernatants of one-round subclones were used to confirm ELISA-based human and cyno TIGIT binding and receptor blocking ability, followed by sequencing and further analysis. After these screenings, 14 clones (90D9, 101E1, 116H8, 118A12, 131A12, 143B6, 167F7, 221F11, 222H4, 327C9, 342A9, 344F2, 349H6 and 350D10) were selected. Sequences of these clones are list in Table 1. Chimeric antibodies fused to human IgG1 Fc of these hybridoma were enerated for further Characterization.

TABLE 1

Antibodies Selected from Screening

| Antibody chain | Sequences* (CDR underlined and bold) | SEQ ID NO: |
|---|---|---|
| 90D9-VH | EVQLQQSGPE LVKPGASVKI SCKTSGYTFT ENTMHWVKQS HGKSLEWIGG INPNQGGNRN NQKFKGKATL TVDKSSSTAY MELRSLTSED SAVYYCARSG LRDYAMDYWG QGTSVTVSS | 1 |
| 90D9-VL | DIVMTQSHKF MSTSVGDRVS ITCKASQHVS TAVVWYQQKP GQSPKLLIYS PSYRYTGVPD RFTGSGSGTD FTFTISSVQA EDLAVYYCQQ HYSTPWTFGG GTKLEIK | 2 |
| 101E1-VH | DVQLQESGPG LVKPSQSLSL TCTVTGYSIT SDYAWNWIRQ FPGNKLEWMG YISYSGNTRY NPSLKSRISI TRDTSKNQFF LQFNSVTTED TATYYCSRKY YGSWFPYWGQ GTLVTVSA | 3 |
| 101E1-VL | DIVMTQSHKF MSTSVGDRVS ITCKASQDVF TAVAWYQQKP GQSPKLLIYS ASYRYTGVPD RFTGSGSGTD FTFTISSVQA EDLAVYYCQQ HYSTPWTFGG GTRLEIK | 4 |
| 116H8-VH | EFQLQQSGPE LVKPGASVKI SCRASGYSFT AYSMNWVQQT NGKSLEWIGV INPKFGTINY NQKFKGKATL TVDQSSSAAY IQLNSLTSED SAVYFCARNG NFAWYFDVWG TGTTVTVSS | 5 |
| 116H8-VL | DIQMTQSPAS LSASVGETVT ITCRASENIF SYLAWYQQKQ GKSPQLLVYN AKTLPEGVPS RFSGSGSGTQ FSLKINSLQS EDFGSYYCQH HYGVPWTFGG GTKLEIK | 6 |
| 118A12-VH | EFQLQQSGPE LVKPGASVKI SCRASGYSFT AYSINWVQQT NGKSLEWIGV INPKFGTINY NQKFKGKATL TVDQSSSAAY MQLNSLTSED SAVYFCARNG NFAWYFDVWG TGTTVTVSS | 7 |
| 118A12-VL | DIQMTQSPAS LSASVGETVT ITCRAGENIY SYLAWYQQKQ GKSPQLLVYN AKTLPEGVPS RFSGSGSGTQ FSLKINSLQS EDFGSYYCQH HYGVPWTFGG GTKLEIK | 8 |
| 131A12-VH | EFQLQQSGPE LVKPGASVKI SCRASGYSFT AYSMNWVQQT NGKSLEWIGV INPKFGTTNY NQKFRDKATL TVDHSSSAAY MQLNSLTSED SAVYFCARNG NFAWYFDVWG TGTTVTVSS | 9 |
| 131A12-VL | DIQMTQSPAS LSASVGETVT ITCRASENIF SYLAWYQQKQ GKSPQLLAYN AETLAEGVPS RFSGSGSGTQ FSLKISSLQS EDFGSYYCQH HFGVPWTFGG GTNLEIK | 10 |
| 143B6-VH | EVQLVESGGG LVMPGGSLKL SCAASGFTFS GFVMSWVRQT PEKRLEWVAT INDAGTYTYY SDNLKGRFTI SRDNAKNNLY LQMSHLKSED AGMYYCARDG GLRAWFPYWG PGTLVTVSA | 11 |
| 143B6-VL | DIQLTQSPAS LSASVGETVT ITCRASENIY SYLAWYQLKQ GKSPQLLVFN TKTLAEGVPS RFSGSGSGTQ FSLRIDSLQL EDFGSFYCQH HIGSPRTFGG GTTLEIR | 12 |
| 167F7-VH | EFQLQQSGPE LVKPGASVKI SCRASGYSFT AYSMNWVQQT NGKSLEWIGV INPKFGTINY NQKFKDKATL TVDHSSSAAY MQLNSLTSED SAVYFCARNG NFAWYFDVWG TGTTVTVSS | 13 |
| 167F7-VL | DIQMTQSPAS LSASVGETVT ITCRASESIF SYLAWYQQKQ GKSPQLLAYN AETLAEGVPS RFSGSGSGTQ FSLKINSLQS EDFGIYYCQH HFGVPWTFGG GTKLEIK | 14 |
| 221F11-VH | EIQLQQTGPE LVKPGASVNI SCKASGYSFT DYIMIWVKQS HGKSLEWIGN IHPYFGNSHY NLKFKGKATL TVDKSSTTAY MQLNSLTSED SAVYYCARRG ITSAHFDYWG QGTTLTVSS | 15 |

TABLE 1-continued

Antibodies Selected from Screening

| Antibody chain | Sequences* (CDR underlined and bold) | SEQ ID NO: |
|---|---|---|
| 221F11-VL | DIVLTQSPAS LAVSLGQRAT ISCRASKSVS TSGYSYMHWY QQKPGQPPKL LIYRASNLES GVPARFSGSG SGTDFTLNIH PVEEEDAATY YCQHSGDLPW TFGGGTKLEI K | 16 |
| 222H4-VH | EVQLQQSGPE LVKPGASVKI SCKTSGYTFS DYTLHWVKQS HGKNLEWIGG FNPNNGGTNY NQKFKVKASL TIDKSSNTVY MELRSLSSED SAVYYCARNW AFDYWGQGTT LTVSS | 17 |
| 222H4-VL | DIVMTQSHKI MSTSLGDRVN ITCKASQHVS TAVAWYQQRP GQSPRLLIYS ASYRHTGVPD RFTGSGSGTD ITFTISSVQT EDLAVYYCQQ YYTTPWTFGG GTKLEIK | 18 |
| 327C9-VH | QIQLVQSGPE LKKPGETVKI SCKASGYTFT AYGMSWVKQT PGKGLKWMGW INTYSGVPTY ADDFKGRFAF SLETSASTAY LQINNLKNED TATYFCTRGD TGGYWGQGAT LTVSS | 19 |
| 327C9-VL | QIVLTQSPAI MSASLGEEIT LTCSARSSVS DMHWYQQKSG TSPKLLIYST SNLASGVPSR FSGSGSGTFF SLTISSVEAE DAADYYCHQW GGYPTFGGGT KLEIK | 20 |
| 342A9-VH | QIQLVQSGPE LKKPGETVKI SCKASGYTFT AYGMGWVKQA PGKGLKWMGW INTYSGVPTY ADDFKGRFAF SLESSASTAY LQINNLKNED TATYFCARGI YFGNYFDYWG QGTTLTVSS | 21 |
| 342A9-VL | DIQMTQSPAS LSASVGETVT ITCRASEIIY TFLAWYQQKQ GKSPQLLVYN ANTLAEGVPS RFSGSGSGTQ FSLKINSLQP EDFGSYYCQH HYGSPYTFGGG GTTLEIK | 22 |
| 344F2-VH | QIQLIQSGPE VKKPGETVKI SCKASGYTFT TYAMTWVKQA AGKGLKWMGW IHTYSGVPTY VDDFKGRFAF SLDTSANTAY LQINNLKNED TATYFCARYD GPLYAMDFWG QGTSVTVSS | 23 |
| 344F2-VL | QIVLTQSPAI MSASPGEKVT ISCSASSSVS YMFWYQQKPG SSPKSWIYRT SNLASGVPGR FSGSGSGTSY SLTISSMEAE DAATYYCQQY HSYFPTFGGG TKLEIK | 24 |
| 349H6-VH | DVQLQESGPG MVKPSQSLSL TCTVTGYSIT SGYDWHWIRH FPGNKLEWMG FISDSGSTKY NPSLKSRISI THDTSKNHFF LKLNSVTSED TATYYCARGS YWYFDVWGTG TTVTVSS | 25 |
| 349H6-VL | DIQMTQSPAS LSASVGETVT ITCRASENIY SYLAWYQQKQ GKSPQLLVNN AKTLAEGVSS RFSGSGSGTQ FSLKINSLQP EDFGSYYCQH HYGNPLMFGA GTKLELK | 26 |
| 350D10-VH | EVKLVESGGA LVQPGGSLKL SCAASGFTFS DYYMYWVRQT PEKRLEWVAS ITKGGGSTYY PDTLKGRFTI SRDNAKNTLY LQMSRLKSED TDMYYCARQS SYDFVMDYWG QGTSVTVSS | 27 |
| 350D10-VL | DIVMTQSHKF MSTSVGDRVT ITCKASQDVD TAVAWYQQKP GQSPKLLIYW ASARHTGVPD RFTGSGSGTD FTLTISNVQS EDLADYFCQQ YSNYPLTFGV GTKLELK | 28 |

*Some amino acids from the original mouse sequences were mutated to increase stability of the antibody (e.g., some N were mutated to Q or S to avoid deamidation or glycosylation).

Example 2

Binding Properties of Anti-TIGIT Mouse Monoclonal Antibodies

This example tested the binding properties of the anti-TIGIT mouse antibodies to the TIGIT proteins.

The results of the ELISA assays are summarized in Table 2, which shows $EC_{50}$ of binding to human and cyno TIGIT protein. The results showed that, among all clones, 90D9, 101E1, 222H4 and 350D10 were the most potent and selective binders to human TIGIT. 90D9 and 350D10 showed comparable binding abilities to cyno TIGIT with those to human TIGIT. 222H4 showed weak binding to cyno TIGIT protein. 101E1 did not bind to cyno TIGIT protein. Effective cyno TIGIT binding has added value, as it can be helpful for in vivo toxicity study.

TABLE 2

| | Binding properties | | | | |
|---|---|---|---|---|---|
| | $EC_{50}$ | | | $EC_{50}$ | |
| Antibody | Human TIGIT | Cyno TIGIT | Antibody | Human TIGIT | Cyno TIGIT |
| 90D9 | 0.021 | 0.064 | 221F11 | 0.052 | N.B. |
| 101E1 | 0.019 | N.B. | 222H4 | 0.029 | 4.614 |
| 116H8 | 0.059 | N.B. | 327C9 | 0.084 | 0.116 |
| 118A12 | 0.045 | 1.195 | 342A9 | 0.056 | 0.093 |
| 131A12 | 0.151 | N.B. | 344F2 | 0.039 | 0.095 |

TABLE 2-continued

Binding properties

| | $EC_{50}$ | | | $EC_{50}$ | |
|---|---|---|---|---|---|
| Antibody | Human TIGIT | Cyno TIGIT | Antibody | Human TIGIT | Cyno TIGIT |
| 143B6 | 0.209 | N.B. | 349H6 | 0.037 | 0.083 |
| 167F7 | 0.059 | 15.110 | 350D10 | 0.039 | 0.138 |

N.B. = No binding

TIGIT antibody BiaCore™ Biosensing Analysis

The binding of the antibodies to recombinant His-tagged human TIGIT-ECD protein was examined by BiaCore™ biosensing T200 using a capture method. The anti-TIGIT antibodies were captured using anti-human Fc antibody or Protein A which were coated on chip. The serial concentrations of his-tagged human TIGIT-ECD protein (0-8 nM) were injected over capture antibodies at the flow rate of 30 μl/min. The dissociation phases were 600 s or 1200s. The results are shown in Table 3 below. The BiaCore™ biosensing results for the anti-TIGIT antibodies demonstrated that these anti-TIGIT antibodies were high affinity binders to human TIGIT.

TABLE 3

Binding of antibodies to recombinant TIGIT protein

| Antibody | ka (1/Ms) | kd (1/s) | KD (M) |
|---|---|---|---|
| 101E1 | 2.90E+06 | 1.05E−03 | 3.62E−10 |
| 90D9 | 6.19E+05 | 1.56E−04 | 2.52E−10 |
| 167F7 | 4.45E+06 | 1.07E−04 | 2.40E−11 |
| 222H4 | 1.87E+06 | 4.53E−04 | 2.42E−10 |
| 350D10 | 1.87E+06 | 1.54E−04 | 8.22E−11 |

Example 3

In Vitro Functional Assay for Screening Anti-TIGIT Mouse Monoclonal Antibodies It is known that human TIGIT and its counter-receptor CD226 compete to bind to their co-ligand CD155 to deliver negative or positive signaling to T cells respectively, resulting in the inhibition of the proliferation of TIGIT-expressed T cells and cytokine production such as interleukin 2 (IL-2). To evaluate the function of anti-TIGIT antibodies in blocking TIGIT signaling on T cells activation, we established a robust in vitro cell-based functional assay. In brief, human TIGIT and it counter-receptor CD226 were simultaneously overexpressed on Jurkat T cells, an immobilized human T cell line, while their co-ligand human CD155 was enforcedly over-expressed on human Burkitt's lymphoma Raji cells. When these two cell types were cocultured in the presence of super antigen, the negative signaling delivered on Jurkat cells by TIGIT-CD155 ligation inhibit the production of Interleukin 2. When serial diluted anti-TIGIT antibodies were added to the culture systems, antibodies can dose-dependently enhance IL-2 production of Jurkat-TIGIT cells. By utilizing this assay, the chimeric antibodies mentioned above were screened. $EC_{50}$ of these antibodies are listed in Table 4. Among these antibodies, 90D9, 101E1, and 350D10 antibodies showed superior efficacy in enhancing Jurkat cell-mediated IL-2 production. Thus, 90D9, 101E1, and 350D10 were selected for humanization and further characterization.

TABLE 4

Functional assay of the antibodies

| Antibody | $EC_{50}$ | Antibody | $EC_{50}$ |
|---|---|---|---|
| 90D9 | 4.429 | 221F11 | 54.260 |
| 101E1 | 2.067 | 222H4 | 5.572 |
| 116H8 | 2.472 | 327C9 | 95.180 |
| 118A12 | 1.437 | 342A9 | 15.630 |
| 131A12 | 4.010 | 344F2 | 9.899 |
| 143B6 | 100.800 | 349H6 | 60.360 |
| 167F7 | 2.864 | 350D10 | 3.947 |

Example 4

Mouse mAb Humanization and Affinity Maturation

A. 90D9

The mouse antibody 90D9 variable region genes were employed to create a humanized MAb. In the first step of this process, the amino acid sequences of the VH and VK of 90D9 were compared against the available database of human Ig gene sequences to identify the overall best-matching human germline Ig gene sequences. For the heavy chain, the closest human match was the IGHV1-3*01 gene. For the light chain, the best human match was the IGKV1-39*01 gene.

Humanized variable domain sequences were then designed where the CDR1 (SEQ ID NO: 29), 2 (SEQ ID NO: 30), and 3 (SEQ ID NO: 31) sequences of the 90D9 VH were grafted onto framework sequences of the IGHV1-3*01 gene and the CDR1 (SEQ ID NO: 32), 2 (SEQ ID NO: 33) and 3 (SEQ ID NO: 34) of the 90D9 light chain were grafted onto framework sequences of the IGKV1-39*01 gene. A 3D model was then generated to determine if there were any framework positions where replacing the mouse amino acid to the human amino acid could affect binding and/or CDR conformation. In the case of the heavy chain, K12, V20, A24, R38, M48, V68, I70, R72 and T91 (Kabat numbering) in human framework was identified and subjected to back-mutations to their moue counterpart amino acid i.e.: K12V, V20L, A24T, R38K, M48I, V68A, I70L, R72V and T91S. In the case of the light chain, A13, L73, L78 and V104 (Kabat numbering) in human framework was identified and subjected to back-mutation to their moue counterpart amino acid i.e.: A13T, L73F, L78V and V104L.

TABLE 5

90D9 sequences and CDRs

| Antibody chain or domain | Sequences (CDR underlined and bold) | SEQ ID NO: |
|---|---|---|
| 90D9 VH | EVQLQQSGPE LVKPGASVKI SCKTSGYTFT ENTMHWVKQS HGKSLEWIGG INPNQGGNRN NQKFKGKATL TVDKSSSTAY MELRSLTSED SAVYYCARSG LRDYAMDYWG QGTSVTVSS | 1 |

TABLE 5-continued

90D9 sequences and CDRs

| Antibody chain or domain | Sequences (CDR underlined and bold) | SEQ ID NO: |
|---|---|---|
| 90D9 VL | DIVMTQSHKF MSTSVGDRVS ITCKASQHVS TAVVWYQQKP GQSPKLLIYS PSYRYTGVPD RFTGSGSGTD FTFTISSVQA EDLAVYYCQQ HYSTPWTFGG GTKLEIK | 2 |
| CDRH1 | ENTMH | 29 |
| CDRH2 | GINPNQGGNR NNQKFKG | 30 |
| CDRH3 | SGLRDYAMDY | 31 |
| CDRL1 | KASQHVSTAV V | 32 |
| CDRL2 | SPSYRYT | 33 |
| CDRL3 | QQHYSTPWT | 34 |

The humanized sequences are listed in Table 6: 90D9-VH1, 90D9-VH2, 90D9-VH3, 90D9-VH4, 90D9-VL1, 90D9-VL2, 90D9-VL3, and 90D9-VL4.

33*01/JK2 gene. Humanized variable domain sequences were then designed where the CDR1 (SEQ ID NO: 43), 2 (SEQ ID NO: 44), and 3 (SEQ ID NO: 45) sequences of the

TABLE 6

Humanized sequences

| Antibody chain | Sequences (CDR italic; back mutations bold and underlined) | SEQ ID NO: |
|---|---|---|
| 90D9-VH1 | QVQLVQSGAE VKKPGASVKV SCK*ASGYTFT ENTMH*WVRQA PGQRLEWMGG *INPNQGGNRN NQKFKG*RVTI TRDTSASTAY MELSSLRSED TAVYYCAR*SG LRDYAMDY*WG QGTLVTVSS | 35 |
| 90D9-VH2 | QVQLVQSGAE VVKPGASVKV SCKTS*GYTFT ENTMH*WVRQA PGQRLEWMGG *INPNGGNRN NQKFKG*RVTI TVDTSASTAY MELSSLRSED TAVYYCAR*SG LRDYAMDY*WG QGTLVTVSS | 36 |
| 90D9-VH3 | QVQLVQSGAE VVKPGASVKV SCKTS*GYTFT ENTMH*WVKQA PGQRLEWIGG *INPNQGGNRN NQKFKG*RVTI TVDTSASTAY MELSSLRSED SAVYYCAR*SG LRDYAMDY*WG QGTLVTVSS | 37 |
| 90D9-VH4 | QVQLVQSGAE VVKPGASVKI SCKTS*GYTFT ENTMH*WVKQA PGQRLEWIGG *INPNQGGNRN NQKFKG*RATL TVDTSASTAY MELSSLRSED SAVYYCAR*SG LRDYAMDY*WG QGTLVTVSS | 38 |
| 90D9-VL1 | DIQMTQSPSS LSASVGDRVT ITC*KASQHVS TAVV*WYQQKP GKAPKLLIY*S PSYRYT*GVPS RFSGSGSGTD FTLTISSLQP EDFATYYC*QQ HYSTPWT*FGQ GTKVEIK | 39 |
| 90D9-VL2 | DIQMTQSPSS LSTSVGDRVT ITC*KASQHVS TAVV*WYQQKP GKAPKLLIY*S PSYRYT*GVPS RFSGSGSGTD FTFTISSLQP EDFATYYC*QQ HYSTPWT*FGQ GTKVEIK | 40 |
| 90D9-VL3 | DIQMTQSPSS LSTSVGDRVT ITC*KASQHVS TAVV*WYQQKP GKAPKLLIY*S PSYRYT*GVPS RFSGSGSGTD FTFTISSVQP EDFATYYC*QQ HYSTPWT*FGQ GTKVEIK | 41 |
| 90D9-VL4 | DIQMTQSPSS LSTSVGDRVT ITC*KASQHVS TAVV*WYQQKP GKAPKLLIY*S PSYRYT*GVPS RFSGSGSGTD FTFTISSVQP EDFATYYC*QQ HYSTPWT*FGQ GTKLEIK | 42 |

B. 350D10

The mouse antibody 350D10 variable region genes were employed to create a humanized antibody. In the first step of this process, the amino acid sequences of the VH and VK of 350D10 were compared against the available database of human Ig gene sequences to find the overall best-matching human germline Ig gene sequences. For the heavy chain, the closest human match was the IGHV3-7*01/JH6 gene. For the light chain the closest human match was the IGKV1-33*01/JK2 gene. A 3D model was then generated to determine if there were any framework positions where replacing the mouse amino acid to the human amino acid could affect binding and/or CDR conformation. In the case of the heavy chain, Q3, G44, S82 (Kabat numbering) in 350D10 VH were grafted onto framework sequences of the IGHV3-7*01/JH6 gene and the CDR1 (SEQ ID NO: 46), 2 (SEQ ID NO: 47) and 3 (SEQ ID NO: 48) of the 350D10 light chain were grafted onto framework sequences of the IGKV1-33*01/JK2 gene. A 3D model was then generated to determine if there were any framework positions where replacing the mouse amino acid to the human amino acid could affect binding and/or CDR conformation. In the case of the heavy chain, Q3, G44, S82 (Kabat numbering) in human framework was identified and subjected to back-mutation to their moue counterpart amino acid i.e.: Q3K, G44R, and S82R. In the case of the light chain, Q3, K42, A43, Y87 (Kabat numbering) in human framework was identified and subjected to back-mutation to their moue counterpart amino acid i.e.: Q3V, K42Q, A43S, Y87F.

C. 101E1

The mouse antibody 101E1 variable region genes were employed to create a humanized MAb. In the first step of this process, the amino acid sequences of the VH and VK of 101E1 were compared against the available database of human Ig gene sequences to find the overall best-matching human germline Ig gene sequences. For the heavy chain, the closest human match was the IGHV4-30-4*01 gene. For the light chain the closest human match was the IGKV1-39*01

TABLE 7

350D10 sequences and CDRs

| Antibody chain or domain | Sequences (CDR underlined and bold) | SEQ ID NO: |
|---|---|---|
| 350D10 VH | EVKLVESGGA LVQPGGSLKL SCAASGFTFS DYYMYWVRQT PEKRLEWVAS ITKGGGSTYY PDTLKGRFTI SRDNAKNTLY LQMSRLKSED TDMYYCARQS SYDFVMDYWG QGTSVTVSS | 27 |
| 350D10 VL | DIVMTQSHKF MSTSVGDRVT ITCKASQDVD TAVAWYQQKP GQSPKLLIYW ASARHTGVPD RFTGSGSGTD FTLTISNVQS EDLADYFCQQ YSNYPLTFGV GTKLELK | 28 |
| CDRH1 | DYYMY | 43 |
| CDRH2 | SITKGGGSTY YPDTLKG | 44 |
| CDRH3 | QSSYDFVMDY | 45 |
| CDRL1 | KASQDVDTAV A | 46 |
| CDRL2 | WASARHT | 47 |
| CDRL3 | QQYSNYPLT | 48 |

The humanized sequences are listed in Table 8: 350D10-VH1, 350D10-VH2, 350D10-VH3, 350D10-VH4, 350D10-VL1, 350D10-VL2, 350D10-VL3, and 350D10-VL4.

TABLE 8

Humanized sequences

| Antibody chain | Sequences (CDR italic; back mutations bold and underlined) | SEQ ID NO: |
|---|---|---|
| 350D10-VH1 | EVQLVESGGG LVQPGGSLRL SCAASGFTFS *DYYMY*WVRQA PGKGLEWVA*S ITKGGGSTYY PDTLKG*RFTI SRDNAKNSLY LQMNSLRAED TAVYYCAR*QS SYDFVMDY*WG QGTTVTVSS | 49 |
| 350D10-VH2 | EVKLVESGGG LVQPGGSLRL SCAASGFTFS *DYYMY*WVRQA PGKGLEWVA*S ITKGGGSTYY PDTLKG*RFTI SRDNAKNSLY LQMNRLRAED TAVYYCAR*QS SYDFVMDY*WG QGTTVTVSS | 50 |
| 350D10-VH3 | EVQLVESGGG LVQPGGSLRL SCAASGFTFS *DYYMY*WVRQA PGKRLEWVA*S ITKGGGSTYY PDTLKG*RFTI SRDNAKNSLY LQMNSLRAED TAVYYCAR*QS SYDFVMDY*WG QGTTVTVSS | 51 |
| 350D10-VH4 | EVKLVESGGG LVQPGGSLRL SCAASGFTFS *DYYMY*WVRQA PGKRLEWVA*S ITKGGGSTYY PDTLKG*RFTI SRDNAKNSLY LQMNRLRAED TAVYYCAR*QS SYDFVMDY*WG QGTTVTVSS | 52 |
| 350D10-VL1 | DIQMTQSPSS LSASVGDRVT ITCK*ASQDVD TAVA*WYQQKP GKAPKLLIY*W ASARHT*GVPS RFSGSGSGTD FTFTISSLQP EDIATYYC*QQ YSNYPLT*FGQ GTKLEIK | 53 |
| 350D10-VL2 | DIVMTQSPSS LSASVGDRVT ITCK*ASQDVD TAVA*WYQQKP GKAPKLLIY*W ASARHT*GVPS RFSGSGSGTD FTFTISSLQP EDIATYYC*QQ YSNYPLT*FGQ GTKLEIK | 54 |
| 350D10-VL3 | DIQMTQSPSS LSASVGDRVT ITCK*ASQDVD TAVA*WYQQKP GQSPKLLIY*W ASARHT*GVPS RFSGSGSGTD FTFTISSLQP EDIATYFC*QQ YSNYPLT*FGQ GTKLEIK | 55 |
| 350D10-VL4 | DIVMTQSPSS LSASVGDRVT ITCK*ASQDVD TAVA*WYQQKP GQSPKLLIY*W ASARHT*GVPS RFSGSGSGTD FTFTISSLQP EDIATYFC*QQ YSNYPLT*FGQ GTKLEIK | 56 | gene. Humanized variable domain sequences were then designed where the CDR1 (SEQ ID NO: 57), 2 (SEQ ID NO: 58), and 3 (SEQ ID NO: 59) sequences of the 101E1 VH were grafted onto framework sequences of the IGHV4-30-4*01 gene and the CDR1 (SEQ ID NO: 60), 2 (SEQ ID NO: 61) and 3 (SEQ ID NO: 62) of the 101E1 light chain were grafted onto framework sequences of the IGKV1-39*01 gene. A 3D model was then generated to determine if there were any framework positions where replacing the mouse amino acid to the human amino acid could affect binding and/or CDR conformation. In the case of the heavy chain, I49, V68, V72, L83 and A97 (Kabat numbering) in human framework was identified and subjected to back-mutation to their moue counterpart amino acid i.e.: I49M, V68I, V72R, L83F and A97S. In the case of the light chain, A13, L73 and L78 (Kabat numbering) in human framework was identified and subjected to back-mutation to their moue counterpart amino acid i.e.: A13T, L73F and L78V.

TABLE 9

101E1 sequences and CDRs

| Antibody chain or domain | Sequences (CDR underlined and bold) | SEQ ID NO: |
|---|---|---|
| 101E1 VH | DVQLQESGPG LVKPSQSLSL TCTVTGYSIT SDYAWNWIRQ FPGNKLEWMG YISYSGNTRY NPSLKSRISI TRDTSKNQFF LQFNSVTTED TATYYCSRKY YGSWFPYWGQ GTLVTVSA | 3 |
| 101E1 VL | DIVMTQSHKF MSTSVGDRVS ITCKASQDVF TAVAWYQQKP GQSPKLLIYS ASYRYTGVPD RFTGSGSGTD FTFTISSVQA EDLAVYYCQQ HYSTPWTFGG GTRLEIK | 4 |
| CDRH1 | SDYAW N | 57 |
| CDRH2 | YISYSGNTRY NPSLKS | 58 |
| CDRH3 | KYYGSWFPY | 59 |
| CDRL1 | KASQDVFTAV A | 60 |
| CDRL2 | SASYRYT | 61 |
| CDRL3 | QQHYSTPWT | 62 |

The humanized sequences are listed in Table 10: 101E1-VH1, 101E1-VH2, 101E1-VH3, 101E1-VH4, 101E1-VL1, 101E1-VL2, 101E1-VL3, and 101E1-VL4.

TABLE 10

Humanized sequences

| Antibody chain | Sequences (CDR italic; back mutations bold and underlined) | SEQ ID NO: |
|---|---|---|
| 101E1-VH1 | QVQLQESGPG LVKPSQTLSL TCTVSGYSIT *SDYAWN*WIRQ PPGKGLEWIG *YISYSGNTRY NPSLKS*RVTI SVDTSKNQFS LKLSSVTAAD TAVYYCAR*KY YGSWFPY*WGQ GTLVTVSS | 63 |
| 101E1-VH2 | QVQLQESGPG LVKPSQTLSL TCTVSGYSIT *SDYAWN*WIRQ PPGKGLEWMG *YISYSGNTRY NPSLKS*RVTI SRDTSKNQFS LKLSSVTAAD TAVYYCAR*KY YGSWFPY*WGQ GTLVTVSS | 64 |
| 101E1-VH3 | QVQLQESGPG LVKPSQTLSL TCTVSGYSIT *SDYAWN*WIRQ PPGKGLEWIG *YISYSGNTRY NPSLKS*RVTI SRDTSKNQFS LKFSSVTAAD TAVYYCSR*KY YGSWFPY*WGQ GTLVTVSS | 65 |
| 101E1-VH4 | QVQLQESGPG LVKPSQTLSL TCTVSGYSIT *SDYAWN*WIRQ PPGKGLEWMG *YISYSGNTRY NPSLKS*RITI SRDTSKNQFS LKFSSVTAAD TAVYYCSR*KY YGSWFPY*WGQ GTLVTVSS | 66 |
| 101E1-VL1 | DIQMTQSPSS LSASVGDRVT ITC*KASQDVF TAVA*WYQQKP GKAPKLLIY*S ASYRYT*GVPS RFSGSGSGTD FTLTISSLQP EDFATYYC*QQ HYSTPWT*FGQ GTRLEIK | 67 |
| 101E1-VL2 | DIQMTQSPSS LSASVGDRVT ITC*KASQDVF TAVA*WYQQKP GKAPKLLIY*S ASYRYT*GVPS RFSGSGSGTD FTFTISSLQP EDFATYYC*QQ HYSTPWT*FGQ GTRLEIK | 68 |
| 101E1-VL3 | DIQMTQSPSS LSTSVGDRVT ITC*KASQDVF TAVA*WYQQKP GKAPKLLIY*S ASYRYT*GVPS RFSGSGSGTD FTFTISSLQP EDFATYYC*QQ HYSTPWT*FGQ GTRLEIK | 69 |

TABLE 10-continued

Humanized sequences

| Antibody chain | Sequences (CDR italic; back mutations bold and underlined) | SEQ ID NO: |
|---|---|---|
| 101E1-VL4 | DIQMTQSPSS LSTSVGDRVT ITC*KASQDVF TAVAWYQQKP GKAPKLLIYS ASYRYTGVPS* RFSGSGSGTD FTFTISSVQP EDFATYYC*QQ HYSTPWTFGQ* GTRLEIK | 70 |

The humanized VH and VK genes were produced synthetically and then respectively cloned into vectors containing the human gamma 1 and human kappa constant domains. The pairing of the human VH and the human VK created 16 humanized antibodies for each parental antibody.

Affinity Ranking of Humanized Antibodies by BiaCore™ Biosensing

To explore the binding kinetics of the humanized antibody, we performed the affinity ranking (3.125 nM, 12.5 nM, 50 nM for 90D9, 12.5 nM and 25 nM for 350D10, 3.125 nM, 12.5 nM, 50 nM for 101E1) by using BiaCore™ biosensing 8K or BiaCore™ biosensing T200. As shown in the Table 11, 90D9H-3, 90D9H-5, 90D9H-6, 90D9H-7, 350D10H-4, 350D10H-8, 350D10H-12, 350D10H-16, 101E1H-6 and 101E1H-13 showed excellent affinity.

TABLE 11

Affinity testing results

| Ligand | ka (1/Ms) | kd (1/s) | KD (M) |
|---|---|---|---|
| 90D9-chimeric | 1.10E+05 | 3.25E−05 | 2.96E−10 |
| 90D9H-1 | 1.25E+05 | 5.95E−05 | 4.78E−10 |
| 90D9H-2 | 6.96E+04 | 4.22E−05 | 6.07E−10 |
| 90D9H-3 | 1.43E+05 | 5.22E−05 | 3.65E−10 |
| 90D9H-5 | 1.69E+05 | 6.64E−05 | 3.92E−10 |
| 90D9H-6 | 2.77E+05 | 6.82E−05 | 2.46E−10 |
| 90D9H-7 | 2.03E+05 | 6.36E−05 | 3.13E−10 |
| 90D9H-8 | 1.10E+05 | 6.64E−05 | 6.03E−10 |
| 90D9H-9 | 2.19E+05 | 1.06E−04 | 4.84E−10 |
| 90D9H-14 | 1.18E+05 | 4.94E−05 | 4.20E−10 |
| 350D10-chimeric | 2.64E+06 | 1.89E−04 | 7.16E−11 |
| 350D10H-1 | 1.34E+06 | 4.13E−04 | 3.01E−10 |
| 350D10H-2 | 1.74E+06 | 2.70E−04 | 1.55E−10 |
| 350D10H-3 | 1.24E+06 | 1.69E−04 | 1.36E−10 |
| 350D10H-4 | 1.92E+06 | 1.95E−04 | 1.02E−10 |
| 350D10H-5 | 1.18E+06 | 3.50E−04 | 2.95E−10 |
| 350D10H-6 | 1.78E+06 | 2.97E−04 | 1.67E−10 |
| 350D10H-7 | 1.20E+06 | 2.03E−04 | 1.69E−10 |
| 350D10H-8 | 1.74E+06 | 1.91E−04 | 1.10E−10 |
| 350D10H-9 | 1.20E+06 | 2.50E−04 | 2.09E−10 |
| 350D10H-10 | 1.92E+06 | 2.40E−04 | 1.25E−10 |
| 350D10H-11 | 1.62E+06 | 2.07E−04 | 1.28E−10 |
| 350D10H-12 | 1.93E+06 | 2.40E−04 | 1.24E−10 |
| 350D10H-13 | 1.26E+06 | 4.10E−04 | 3.25E−10 |
| 350D10H-14 | 1.80E+06 | 2.62E−04 | 1.46E−10 |
| 350D10H-15 | 1.33E+06 | 2.13E−04 | 1.61E−10 |
| 350D10H-16 | 1.85E+06 | 1.77E−04 | 9.56E−11 |
| 101E1-chimeric | 2.34E+06 | 1.14E−03 | 4.87E−10 |
| 101E1H-6 | 1.02E+06 | 1.76E−03 | 1.72E−09 |
| 101E1H-10 | 7.20E+05 | 1.46E−03 | 2.04E−09 |
| 101E1H-13 | 8.72E+05 | 1.49E−03 | 1.70E−09 |

Example 5

TIGIT Antibody BiaCore™ Biosensing Analysis

The binding of three of the humanized antibodies, referred to as 90D9H, 101E1H, and 350D10H respectively, to recombinant His-tagged human TIGIT-ECD protein was examined by BiaCore™ biosensing T200 using a capture method. The anti-TIGIT antibodies were captured using anti-human Fc antibody or Protein A which were coated on the chip. Serial concentrations of His-tagged human TIGIT-ECD protein (0-8 nM) were injected over capture antibodies at the flow rate of 30 µl/min. The dissociation phases were 600 s or 1200s. The results are shown in Table 12 below. The BiaCore™ biosensing results for the anti-TIGIT antibodies have shown that these anti-TIGIT antibodies are high affinity binders to human TIGIT. As shown in the table, 90D9H, and 350D10H had comparable affinity to their individual parental chimeric antibodies while 101E1H shows slight affinity loss after humanization.

TABLE 12

Binding results

| Ligand | ka (1/Ms) | kd (1/s) | KD (M) |
|---|---|---|---|
| 90D9-chimeric | 4.46E+05 | 1.67E−04 | 3.74E−10 |
| 90D9H | 2.33E+05 | 1.66E−04 | 7.12E−10 |
| 350D10-chimeric | 1.87E+06 | 1.54E−04 | 8.22E−11 |
| 350D10H | 1.50E+06 | 1.59E−04 | 1.06E−10 |
| 101E1-chimeric | 2.90E+06 | 1.05E−03 | 3.62E−10 |
| 101E1H | 5.95E+05 | 1.81E−03 | 3.04E−09 |

Example 6

Binding Properties of Anti-TIGIT Human Monoclonal Antibodies

This example tested the binding properties of the humanized anti-TIGIT antibodies to the TIGIT proteins.

Binding Properties of Anti-TIGIT Monoclonal Antibodies to TIGIT Protein

To evaluate the binding specificity, the 90D9H, 101E1H, and 350D10H monoclonal antibodies were subjected to ELISA binding test for His-tagged human TIGIT and cyno-TIGIT antigens. The results of the ELISA are summarized in FIG. 1, which shows EC50 for binding to human and cyno TIGIT protein, demonstrating that 90D9H, 101E1H, 350D10H are potent and selective binders for human TIGIT. 90D9H and 350D10H show comparable binding ability to cyno TIGIT with that of human TIGIT except 101E1H, who shows no binding to cyno TIGIT protein.

Binding Properties of Anti-TIGIT Human Monoclonal Antibodies to TIGIT Expressed Jurkat Cell Line A TIGIT-overexpressed Jurkat cell line was used to evaluate the binding ability of TIGIT antibodies to cell surface-expressed TIGIT. Humanized antibodies were serially diluted with FACS buffer and incubated with Jurkat-TIGIT-CD226 cells for 30 min on ice. The labeled cells were washed with FACS buffer and subsequently labeled with PE-conjugated anti-human IgG antibodies for 30 min on ice. The resulting cells were washed once with FACS buffer.

Labeled cells were evaluated for fluorescence intensity by flow cytometry in a BD FACSCelesta™. As shown in FIG. 2, 90D9H, 101E1H, and 350D10H can dose-dependently binding to TIGIT expressed on Jurkat cell line.

Figure 3:
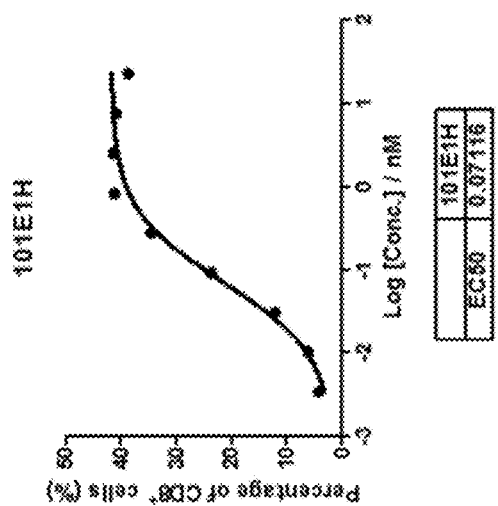
FIG. 3 shows that the 90D9H, 101E1H, and 350D10H antibodies dose-dependently bound to TIGIT expressed on the activated human CD8+ T cells.
Figure 3:
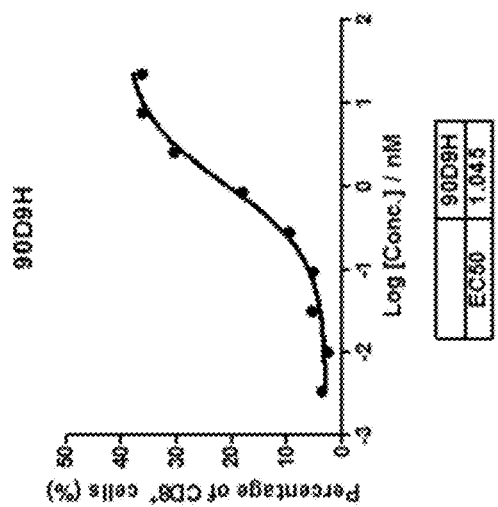
Figure 3:
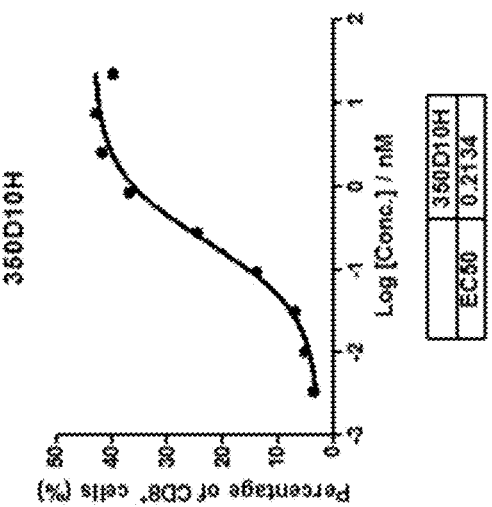

Binding properties of anti-TIGIT antibodies to TIGIT on activated human primary CD8+ T cells TIGIT is expressed on activated or exhausted human T cells. CD8+ T cells were isolated using CD8 magnetic beads. The purified human CD8+ T cells were stimulated with Dynabeads® Human T-Activator CD3/CD28 for 72 hrs. Antibodies were serially diluted with FACS buffer. To assess binding, TIGIT antibodies at various concentrations were then added to the activated human CD8+ T cells for 30 min on ice. The labeled cells were then washed with FACS buffer and subsequently labeled with PE-conjugated anti-human IgG antibodies for 30 min on ice. The resulting cells were washed once with FACS buffer. Labeled cells were evaluated for fluorescence intensity by flow cytometry in a BD FACSCelesta™. As shown in FIG. 3, the 90D9H, 101E1H, and 350D10H antibodies can dose-dependently binding to TIGIT expressed on the activated human CD8+ T cells.

Example 7

Functional Properties of Anti-TIGIT Mouse Monoclonal Antibodies

Blocking the Binding of TIGIT Protein to its Ligand CD155

Figure 4:
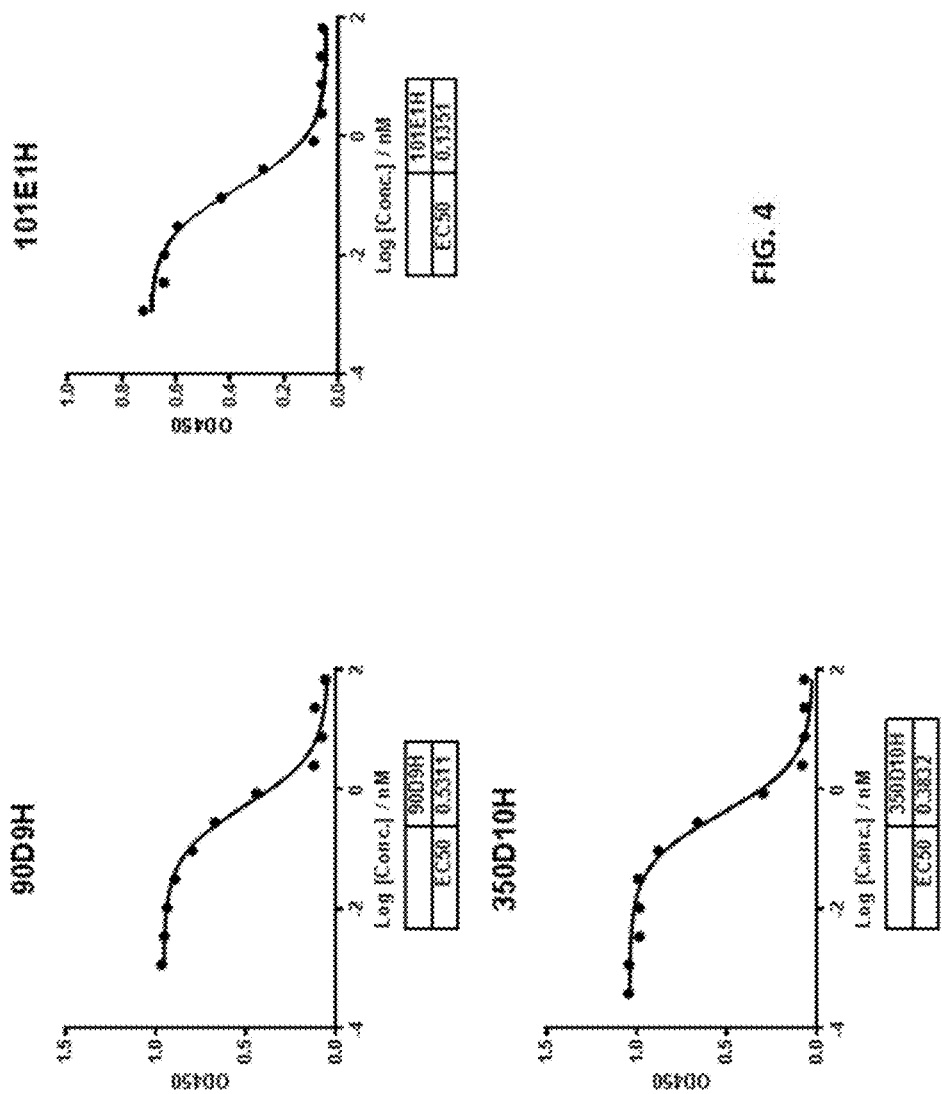
FIG. 4 shows that the 90D9H, 101E1H and 350D10H antibodies dose-dependently inhibited the binding of CD155 to its receptor TIGIT.

To evaluate the ability of anti-TIGIT antibodies to block the binding of TIGIT to its ligand CD155, an ELISA-based receptor blocking assay previously described in Example 1 were used. 90D9H,101E1H and 350D10H antibodies were serially diluted from 10 μg/mL with PBS. As shown in FIG. 4, the 90D9H, 101E1H and 350D10H antibodies can dose-dependently inhibit the binding of CD155 to its receptor TIGIT.

Blocking the Binding of TIGIT Expressed on K562 Cells to its Ligand CD155

Figure 5:
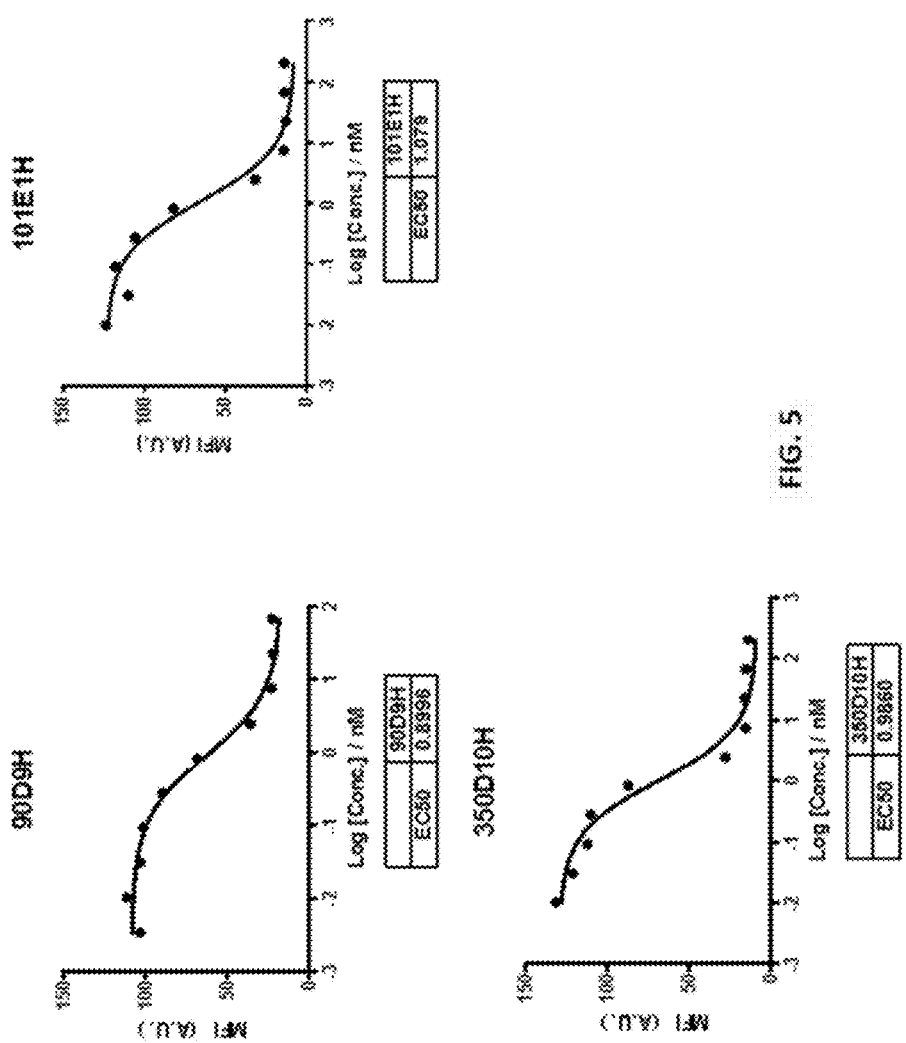
FIG. 5 shows that the 90D9H, 101E1H and 350D10H antibodies dose-dependently inhibited the binding of CD155 to its receptor TIGIT expressed on cell surface.

To evaluate the ability of anti-TIGIT antibodies to block the binding of cell surface TIGIT to its ligand CD155, a cell-based receptor blocking assay was designed. In brief, human TIGIT were overexpressed on human chronic myelogenous leukemia lymphoblast cell line K562 cells. Antibodies were serially diluted from 10 μg/mL with PBS and incubated with TIGIT-overexpressed K562 cells ($1*10^5$ cells/test) for 30 min at 4° C. hCD155-hFc protein (3 μg/mL) was then incubated with antibody-cell complex for 30 min at 4° C. PE-anti-human CD155 antibody (R&D, FAB25301P) was used to detect hCD155 when it bound to TIGIT expressed on cell surface. As shown in FIG. 5, the 90D9H, 101E1H and 350D10H antibodies can dose-dependently inhibit the binding of CD155 to its receptor TIGIT expressed on cell surface.

Figure 6:
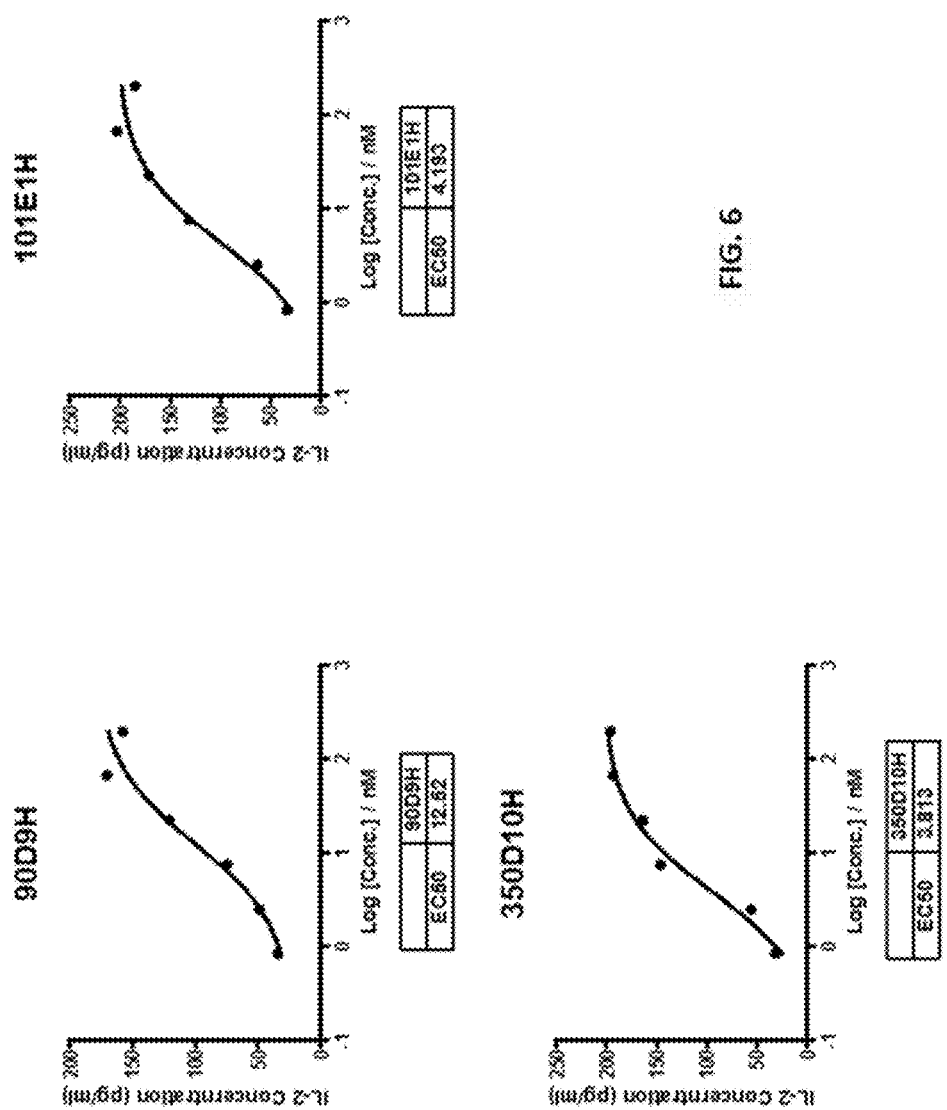
FIG. 6 shows that the 90D9H, 101E1H, and 350D10H antibodies dose-dependently enhanced Jurkat cell-mediated IL-2 production.

Blocking TIGIT-CD155 Signal Mediated IL-2 Production Inhibition by TIGIT Antibodies in Jurkat Functional Assay To evaluate the TIGIT-blocking function of humanized antibodies, in vitro Jurkat functional assay described in Example 3 was used. As described in FIG. 6, the 90D9H, 101E1H, and 350D10H antibodies can dose-dependently enhance Jurkat cell-mediated IL-2 production.

Example 8

Affinity Maturation of 101E1

To optimize the $K_{off}$ of 101E1, this example initiated an affinity maturation procedure. Briefly, paratope mapping by using alanine scanning in the CDR region was performed to identify the key residues that affect antibodies binding to TIGIT or production. Then the CDR amino acids surrounding the key residues were selected to construct NNK library and screened by affinity ranking to identify mutations that improve the off-rate for human TIGIT but do not affect the expression level of the antibody. Mutated Amino acids that could improve $K_{off}$ binding of 101E1 are listed in Table 13. A combinational library that incorporated all the mutant form of these amino acids was constructed and screened. Sequences of lead clones that have lower off-rate for human TIGIT are listed in Table 14. Antibodies of these sequences were generated and affinity ranking was performed by BiaCore™ biosensing T200. The results are listed in Table 15. As described here, 101E1HM-3 shows enhanced $K_{off}$-rate compared with parental antibodies.

TABLE 13

Mutations in 101E1 useful for improving binding

| Residue | Substituted with |
| --- | --- |
| VH-31S | Q, R, or D |
| VH-57N | E, H, A, T, S, V, M, Q, D, or I |
| VH-59R | L, M, P, K, or S |
| VH-66S | N, D, or G |
| VH-100Y | D, or H |
| VH-103S | G |
| VH-107Y | I, V, N, L, S, D, E, R, or Q |
| VL-53Y | N, or H |
| VL-55Y | H, E, C, D, T, K, A, N, Q, P, N, or M |
| VL-56T | N |
| VL-91H | N, P, E, L, S, T, C, R, I, K, F, G, Y, H, or A |

TABLE 14

Lead clones

| Antibody chain | Sequences (mutations bold, CDR residues are underlined) | SEQ ID NO: |
| --- | --- | --- |
| 101E1HM-VH1 | QVQLQESGPG LVKPSQTLSL TCTVSGYSIT DDYAWNWIRQ PPGKGLEWMG YISYSGHTKY NPSLKSRVTI SRDTSKNQFS LKLSSVTAAD TAVYYCARKY YGGWFPRWGQ GTLVTVSS | 71 |
| 101E1HM-VH2 | QVQLQESGPG LVKPSQTLSL TCTVSGYSIT DDYAWNWIRQ PPGKGLEWMG YISYSGNTMY NPSLKSRVTI SRDTSKNQFS LKLSSVTAAD TAVYYCARKY YGGWFPIWGQ GTLVTVSS | 72 |
| 101E1HM-VH3 | QVQLQESGPG LVKPSQTLSL TCTVSGYSIT DDYAWNWIRQ PPGKGLEWMG YISYSGDTKY NPSLKSRVTI SRDTSKNQFS LKLSSVTAAD TAVYYCARKY YGGWFPVWGQ GTLVTVSS | 73 |

TABLE 14-continued

Lead clones

| Antibody chain | Sequences (mutations bold, CDR residues are underlined) | SEQ ID NO: |
|---|---|---|
| 101E1HM-VH4 | QVQLQESGPG LVKPSQTLSL TCTVSGYSIT DDYAWNWIRQ PPGKGLEWMG YISYSGHTRY NPSLKSRVTI SRDTSKNQFS LKLSSVTAAD TAVYYCARKY YGSWFPDWGQ GTLVTVSS | 74 |
| 101E1HM-VH5 | QVQLQESGPG LVKPSQTLSL TCTVSGYSIT DDYAWNWIRQ PPGKGLEWMG YISYSGITRY NPSLKSRVTI SRDTSKNQFS LKLSSVTAAD TAVYYCARKY YGGWFPQWGQ GTLVTVSS | 75 |
| 101E1HM-VL1 | DIQMTQSPSS LSASVGDRVT ITCKASQDVF TAVAWYQQKP GKAPKLLIYS ASYRPTGVPS RFSGSGSGTD FTFTISSLQP EDFATYYCQQ SYSTPWTFGQ GTRLEIK | 76 |
| 101E1HM-VL2 | DIQMTQSPSS LSASVGDRVT ITCKASQDVF TAVAWYQQKP GKAPKLLIYS ASYRHTGVPS RFSGSGSGTD FTFTISSLQP EDFATYYCQQ SYSTPWTFGQ GTRLEIK | 77 |
| 101E1HM-VL3 | DIQMTQSPSS LSASVGDRVT ITCKASQDVF TAVAWYQQKP GKAPKLLIYS ASNRNTGVPS RFSGSGSGTD FTFTISSLQP EDFATYYCQQ QYSTPWTFGQ GTRLEIK | 78 |
| 101E1HM-VL4 | DIQMTQSPSS LSASVGDRVT ITCKASQDVF TAVAWYQQKP GKAPKLLIYS ASYRMTGVPS RFSGSGSGTD FTFTISSLQP EDFATYYCQQ SYSTPWTFGQ GTRLEIK | 79 |
| 101E1HM-VL5 | DIQMTQSPSS LSASVGDRVT ITCKASQDVF TAVAWYQQKP GKAPKLLIYS ASYRDTGVPS RFSGSGSGTD FTFTISSLQP EDFATYYCQQ SYSTPWTFGQ GTRLEIK | 80 |

TABLE 15

Binding results

| Ligand | ka (1/Ms) | kd (1/s) | KD (M) |
|---|---|---|---|
| 101E1H | 7.96E+05 | 1.98E-03 | 2.49E-09 |
| 101E1HM-1 | 4.96E+05 | 1.07E-03 | 2.15E-09 |
| 101E1HM-2 | 1.29E+06 | 1.91E-03 | 1.48E-09 |
| 101E1HM-3 | 1.29E+06 | 7.17E-04 | 5.54E-10 |
| 101E1HM-4 | 1.43E+06 | 4.39E-03 | 3.08E-09 |
| 101E1HM-5 | 1.63E+06 | 2.09E-03 | 1.29E-09 |

Example 9

Figure 7:
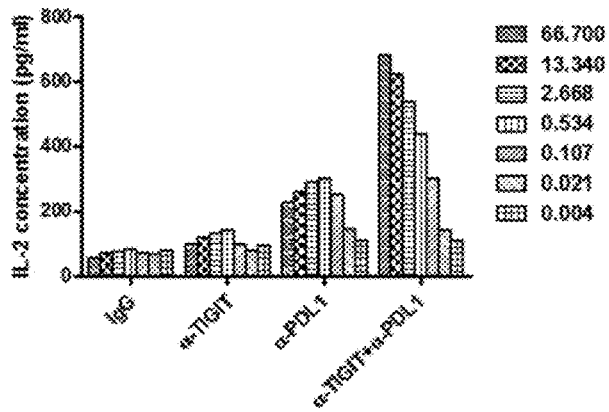
FIG. 7 shows that anti-TIGIT and anti-PD-L1 antibodies synergistically enhanced the production of IL-2.

Synergistic Effect of Anti-TIGIT and Anti-PDL1 Antibodies in In Vitro Cell Based Functional Assay Stimulation of IL2 Release by Jurkat T Cells To evaluate the synergistic effect of anti-TIGIT antibodies and anti-PDL1 antibodies in boosting T cells activation, we established a robust in vitro cell-based functional assay. In brief, human TIGIT, CD226 and PD1 were simultaneously overexpressed on Jurkat T cells, while their individual ligands CD155 and PDL1 were over-expressed on Raji cells. When these two cell types were cocultured in the presence of super antigen, the negative signaling delivered on Jurkat cells by both TIGIT-CD155 and PD1-PDL1 ligation synergistically inhibited the production of IL-2. As shown in FIG. 7, When serial diluted anti-TIGIT or anti-PDL1 antibodies were added to the culture systems, antibodies could mildly and dose-dependently enhance IL-2 production of Jurkat-TIGIT cells. However, combination of anti-TIGIT and anti-PDL1 antibodies significantly enhanced IL-2 production, showing a strong synergistic effect of these two antibodies.

Stimulation of IFN-γ Release by Activated CD8+ T Cells

Figure 8:
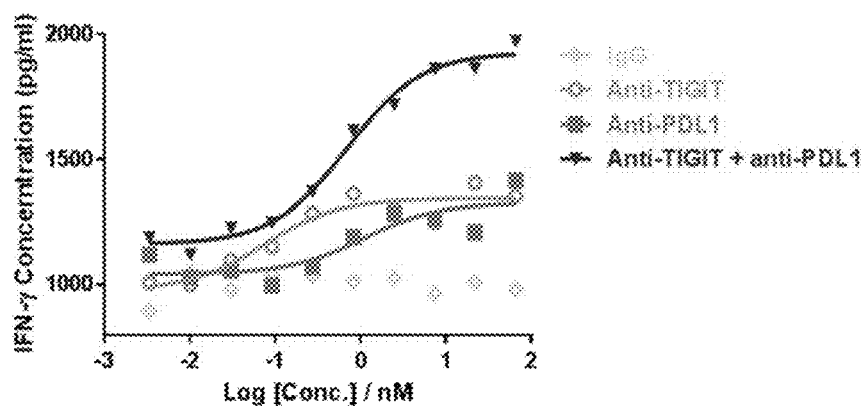
FIG. 8 shows the results of synergistical stimulation of IFN-r production by CD8+ T cells by anti-TIGIT and anti-PDL1 antibodies.
Figure 9:
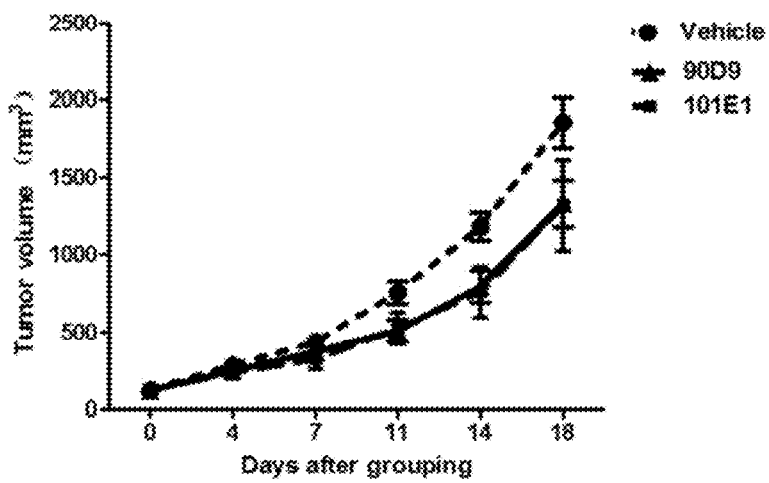
FIG. 9 shows that 90D9 and 101E1 showed mild inhibition of tumor growth.

The synergistic effect of anti-TIGIT antibody and anti-PDL1 antibody on primary CD8+ T cells activation was further studied using PBMCs from healthy donors. In brief, CHO-K1 cells constitutively expressing an engineered T cell receptor (TCR) activator, human CD155 and PDL1 (CHO-TCR-CD155-PDL1 cells) were seeded at a density of 35,000 cells per well and incubated overnight. Purified CD8+ T cells isolated from healthy donors were incubated with CHO-TCR-CD155-PDL1 cells at a density of 50,000 cells per well. Serially diluted anti-TIGIT, anti-PDL1 or the combination of these two antibodies were then added to the co-culture system for 3 days and the culture medium was collected for IFN-γ measurement using a standard ELISA kit. As shown in FIG. 8, while anti-TIGIT or anti-PDL1 antibodies could weakly stimulate IFN-γ production in primary CD8+ T cells in a concentration-dependent manner, the combination of these two antibodies significantly enhanced IFN-γ production, demonstrating a strong synergistic effect of these two antibodies on primary CD8+ T cell activation in vitro.

Example 10

In Vivo Efficacy of Anti-TIGIT Antibody Monotherapy

Mouse colon cancer cell line MC38 cells were grafted subcutaneously (s.c.) into TIGIT humanized C56/BL6 mice. Mice were grouped according to tumor volume when the average tumor volume reached 150±50 mm³ and administered different TIGIT antibodies (10 mg/kg) every three days for 6 times. Tumor volumes were monitored twice a week. As shown in FIG. 9, 90D9 and 101E1 showed mild inhibition of tumor growth (TGI: 30.4% and 30.9%; P value: 0.034 and 0.136 at Day 18 after grouping).

Figure 10:
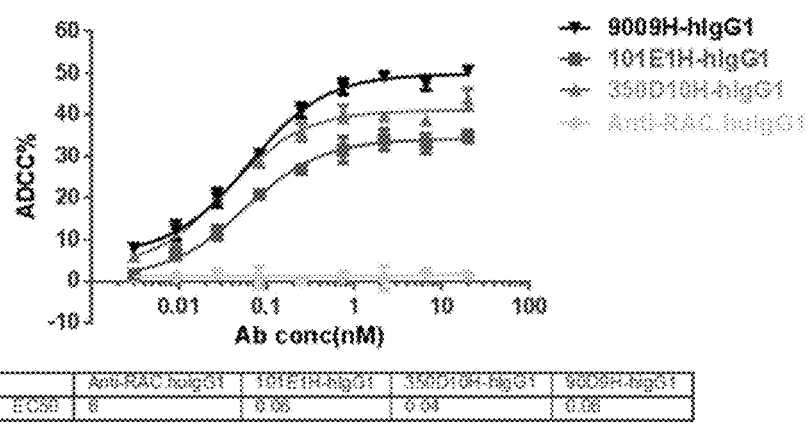
FIG. 10 shows the in vitro cytotoxicity assay measured by lactate dehydrogenase (LDH) release.

Next, we evaluated contribution of ADCC effect on in vivo efficacy of anti-TIGIT antibodies. Before performing in vivo study, the ADCC activities of 90D9, 101E1 and 350D10 with wild type human IgG1 which had a strong ADCC effect in human system were evaluated by an in vitro ADCC assay. In brief, TIGIT-overexpressing Jurkat cells (Jurkat-TIGIT) were used as target cells at a density of 2E4 per well. A human natural killer cell line NK92 cells with enforced expression of the Fcγ receptor CD16a (NK92-CD16a) were used as effector cells. NK92-CD16a were cocultured with Jurkat-TIGIT cells at a ratio of 3:1 for 4 hours. Serially diluted anti-TIGIT antibodies were added to the coculture system. Anti-RAC-hIgG1 antibody was used as a non-relevant negative control. Cytotoxicity was measured by lactate dehydrogenase (LDH) release. As shown in FIG. 10, All of three anti-TIGIT antibodies effectively lysed Jurkat-TIGIT cells with a maximum ADCC activity of 50% and comparable EC50, indicating these antibodies could elicit cytotoxicity on TIGIT-expressing cells in vitro.

Figure 11:
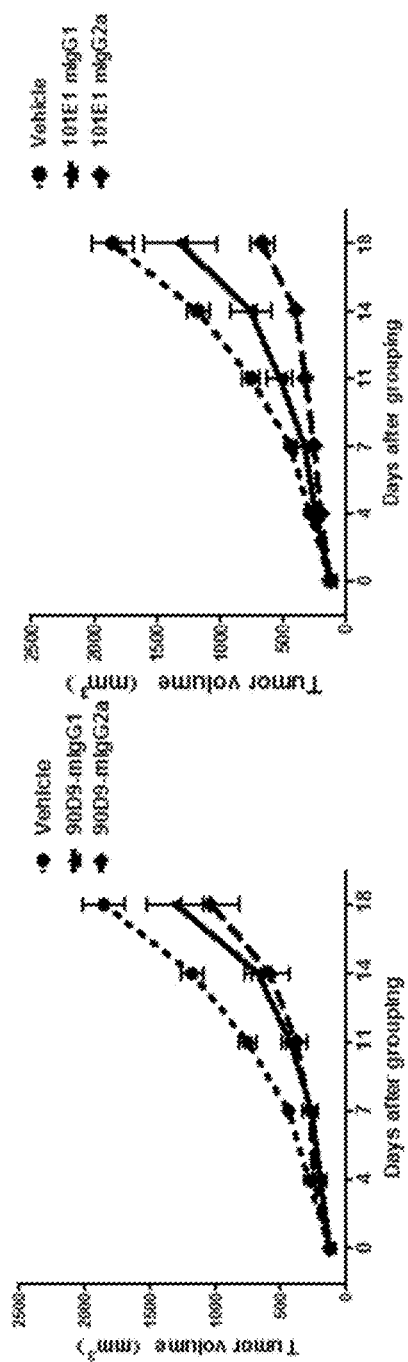
FIG. 11 shows that in vivo efficacy of 90D9 and 101E1 antibodies with (mIgG2a) or without (mIgG1) ADCC effect in an MC38 syngeneic mice model.
Figure 12:
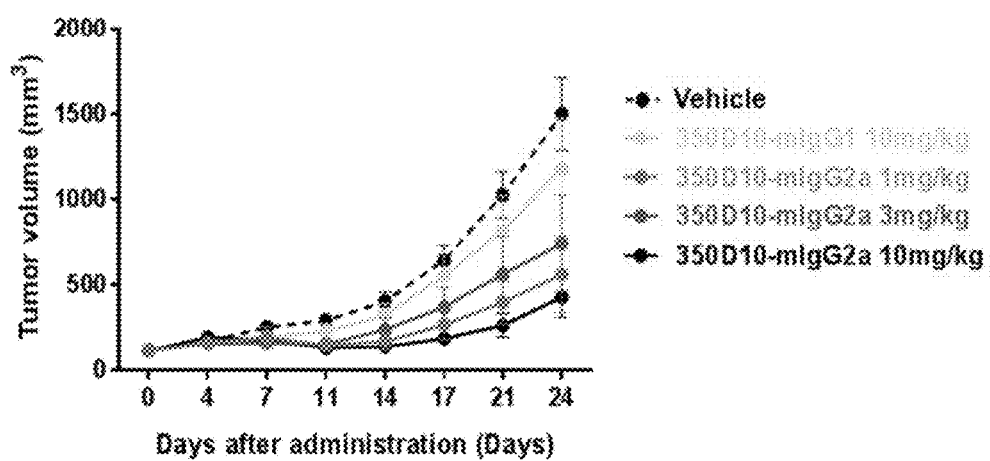
FIG. 12 and FIG. 13 show the in vivo efficacy of different 350D10 antibodies in an MC38 syngeneic mouse model.
Figure 13:
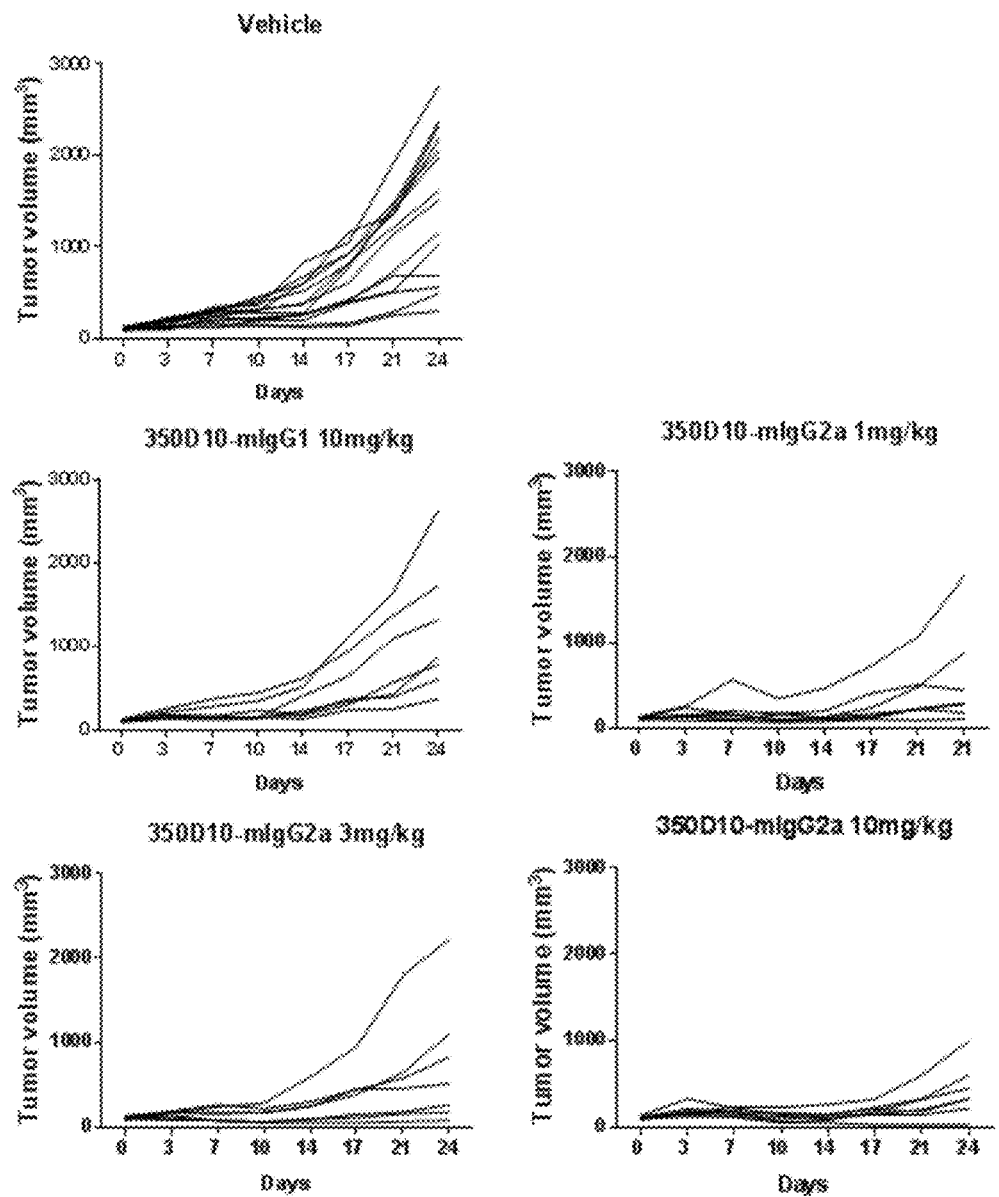

To evaluate the contribution of ADCC effect on in vivo efficacy, mIgG2a which had strong ADCC effect was used as the ADCC-enabled isotype to compare with mIgG1 which was an ADCC-disabled isotype in mouse systems. As shown in FIG. 11, 90D9-mIgG2a showed more potent efficacy in reducing tumor growth compared to 90D9-mIgG1 (TGI: 47.2% vs. 31.7%; P value: 0.012 vs. 0.066). For 101E1, 101E1-mIgG2a showed stronger tumor inhibition effect than 101E1-mIgG1(TGI: 68.8% vs. 30.9%, P value: 0 vs. 0.136). To evaluate the relationship of dose and efficacy, multiple doses of 350D10-mIgG2a (1, 3 and 10 mg/kg) were administrated in the MC38 mice model. As shown in FIG. 12 and FIG. 13, mono-treatment of 350D10-mIgG2a at all three dose groups significantly suppressed tumor growth compared to vehicle, achieving maximal 77.5% tumor growth inhibition (TGI) at 10 mg/kg 24 days after first dosing (P value<0.05, Table 16). In contrast, 350D10-mIgG1 treatment showed very weak tumor inhibition, indicating the importance of ADCC function for anti-tumor efficacy by TIGIT antibodies.

TABLE 16

Effect of anti-TIGIT antibodies on tumor volume in MC38 mice model

| Antibody | Tumor volume (mm³) [a] | | TGI (%) | P [b] |
|---|---|---|---|---|
| | Before dosing | 24 days after first dosing | | |
| Vehicle | 114 ± 3 | 1498 ± 212 | — | — |
| 350D10-mIgG1 10 mg/kg | 114 ± 5 | 1181 ± 296 | 22.9 | 0.397 |
| 350D10-mIgG2a 1 mg/kg | 114 ± 5 | 561 ± 224 | 67.7 | 0.013 |
| 350D10-mIgG2a 3 mg/kg | 114 ± 6 | 743 ± 281 | 54.6 | 0.0497 |
| 350D10-mIgG2a 10 mg/kg | 114 ± 6 | 426 ± 117 | 77.5 | 0.003 |

Note:
[a] Mean ± SD;
[b] Statistical analysis of tumor volume between antibody treatment groups and vehicle group at 24 days after first dosing by Student's t-test.
P < 0.05 is considered statistically significant.

Figure 14:
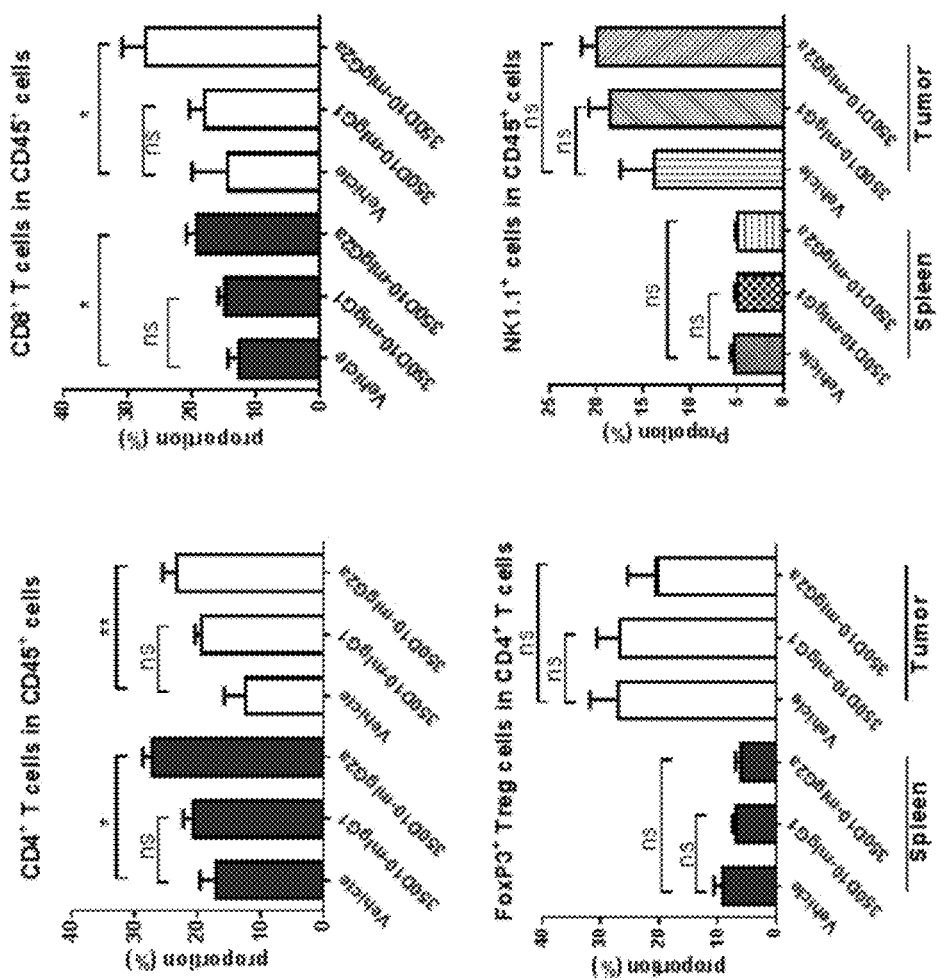
FIG. 14 shows the percentages of splenic and tumor infiltrating CD4+ T and CD8+ T cells afteranti-TIGIT or control antibody treated groups.

To evaluate the mechanisms of anti-TIGIT antibody-mediated tumor growth inhibition, tumor infiltrating cells were isolated from tumor tissue of the vehicle, 350D10-mIgG1 and 350D10-mIgG2a 10 mg/kg groups at the end of the study (FIG. 12). Percentages of splenic and tumor infiltrating CD4+ T cells, CD8+ T cells, CD4+ regulatory T cells and NK cells were analyzed by FACS. As shown in FIG. 14, CD4+ T and CD8+ T cells were significantly enriched in both spleen and tumor tissue of 350D10-mIgG2a-treated group compared with the vehicle and 350D10-mIgG1 groups. NK cells were not significantly changed among three groups. Interestingly, we observed a mild decrease of CD4+ Treg cells in 350D10-mIgG2a groups compared with other two groups, although this change was not statistically significant. These data indicate anti-TIGIT antibody with ADCC function could modulate the tumor-microenvironment to reduce tumor growth through promoting infiltration of anti-tumor CD4+ T and CD8+ T cells.

Example 11

In Vivo Efficacy of Combo-Therapy of Anti-TIGIT and Anti-PDL1 Antibodies

Figure 15:
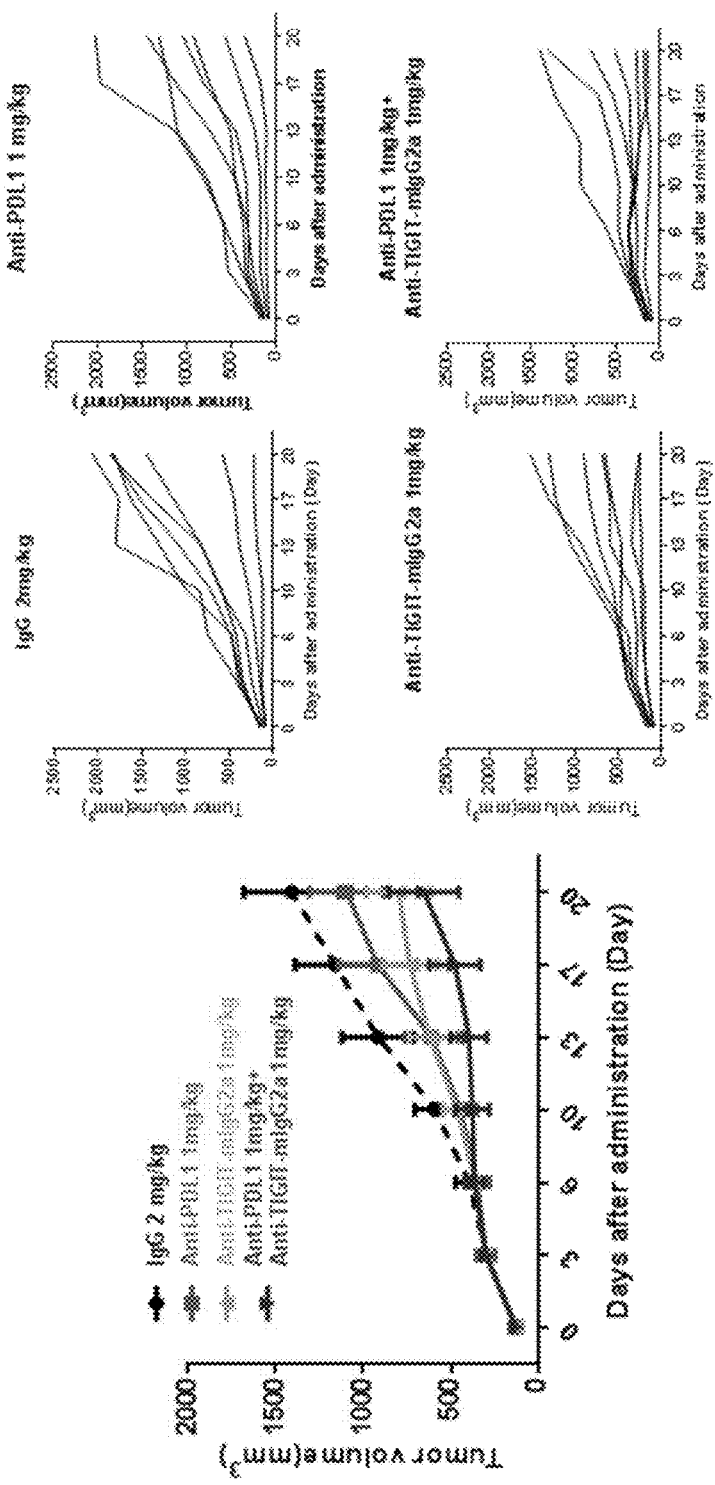
FIG. 15 shows that combo-therapy of anti-TIGIT or anti-PDL1 antibodies synergistically inhibited tumor growth compared with mono-therapies.

To evaluate the synergistic effect of anti-TIGIT and anti-PDL1 antibodies in vivo, MC38 tumor cells with humanized PDL1 were transplanted into PDL1 and TIGIT double-humanized mice. When the average tumor volumes reached 100 mm³, anti-TIGIT, anti-PDL1 or combination of these two antibodies were administrated intraperitoneally (i.p.) at 1 mg/kg every three days for six times. The results showed that monotherapies of anti-TIGIT or anti-PDL1 antibodies mildly inhibited tumor growth (TGI: 47.5% and 24.5%) compared to IgG group at Day 20 after first dosing (FIG. 15). Combination of these two antibodies showed significant synergistic effect in controlling tumor growth compared to IgG group (TGI: 58.5%, P value: 0.045), indicating the potential benefit of the combo-therapy in the future immunotherapy.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. An antibody or fragment thereof having specificity to a human T cell immunoreceptor with Ig and ITIM domains (TIGIT) protein, wherein the antibody or fragment thereof comprises a heavy chain variable region comprising heavy chain complementarity determining regions HCDR1, HCDR2, and HCDR3, and a light chain variable region comprising light chain complementarity determining regions LCDR1, LCDR2, and LCDR3, wherein the HCDR1 comprises the amino acid sequence of DYYMY (SEQ ID NO: 43), the HCDR2 comprises the amino acid sequence of SITKGGGSTYYPDTLKG (SEQ ID NO: 44), the HCDR3 comprises the amino acid sequence of QSSYDFVMDY (SEQ ID NO: 45), the LCDR1 comprises the amino acid sequence of KASQDVDTAVA (SEQ ID NO: 46), the LCDR2 comprises the amino acid sequence of WASARHT (SEQ ID NO: 47), and the LCDR3 comprises the amino acid sequence of QQYSNYPLT (SEQ ID NO: 48).

2. The antibody or fragment thereof of claim 1, which is humanized and wherein the heavy chain variable region comprises one or more back mutations selected from the group consisting of 3K, 44R, and 82R, according to Kabat numbering, and combinations thereof.

3. The antibody or fragment thereof of claim 1, which is humanized and wherein the light chain variable region comprises one or more back mutations selected from the group consisting of 3V, 42Q, 43S, and 87F, according to Kabat numbering, and combinations thereof.

4. The antibody or fragment thereof of claim 1, comprising a heavy chain variable region comprising an amino acid sequence selected from the group consisting of SEQ ID NO: 27, and 49-52, or an amino acid sequence having at least 90% sequence identity to an amino acid sequence selected from the group consisting of SEQ ID NO: 27, and 49-52.

5. The antibody or fragment thereof of claim 1, comprising a light chain variable region comprising an amino acid sequence selected from the group consisting of SEQ ID NO: 28, and 53-56, or an amino acid sequence having at least 90% sequence identity to an amino acid sequence selected from the group consisting of SEQ ID NO: 28, and 53-56.

6. The antibody or fragment thereof of claim 1, which is bispecific.

7. An isolated cell comprising one or more polynucleotide encoding the antibody or fragment thereof of claim 1.

* * * * *

SEQUENCE LISTING

<160> NUMBER OF SEQ ID NOS: 80

<210> SEQ ID NO 1
<211> LENGTH: 119
<212> TYPE: PRT
<213> ORGANISM: Artificial Sequence
<220> FEATURE:

<223> OTHER INFORMATION: Synthetic

<400> SEQUENCE: 1

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Asn
            20                  25                  30

Thr Met His Trp Val Lys Gln Ser His Gly Lys Ser Leu Glu Trp Ile
        35                  40                  45

Gly Gly Ile Asn Pro Asn Gln Gly Gly Asn Arg Asn Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Gly Leu Arg Asp Tyr Ala Met Asp Tyr Trp Gly Gln Gly
            100                 105                 110

Thr Ser Val Thr Val Ser Ser
        115
```

<210> SEQ ID NO 2
<211> LENGTH: 107
<212> TYPE: PRT
<213> ORGANISM: Artificial Sequence
<220> FEATURE:
<223> OTHER INFORMATION: Synthetic

<400> SEQUENCE: 2

```
Asp Ile Val Met Thr Gln Ser His Lys Phe Met Ser Thr Ser Val Gly
1               5                   10                  15

Asp Arg Val Ser Ile Thr Cys Lys Ala Ser Gln His Val Ser Thr Ala
            20                  25                  30

Val Val Trp Tyr Gln Gln Lys Pro Gly Gln Ser Pro Lys Leu Leu Ile
        35                  40                  45

Tyr Ser Pro Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105
```

<210> SEQ ID NO 3
<211> LENGTH: 118
<212> TYPE: PRT
<213> ORGANISM: Artificial Sequence
<220> FEATURE:
<223> OTHER INFORMATION: Synthetic

<400> SEQUENCE: 3

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Asn Thr Arg Tyr Asn Pro Ser Leu
```

```
                 50                  55                  60
Lys Ser Arg Ile Ser Ile Thr Arg Asp Thr Ser Lys Asn Gln Phe Phe
 65                  70                  75                  80

Leu Gln Phe Asn Ser Val Thr Thr Glu Asp Thr Ala Thr Tyr Tyr Cys
                     85                  90                  95

Ser Arg Lys Tyr Tyr Gly Ser Trp Phe Pro Tyr Trp Gly Gln Gly Thr
                100                 105                 110

Leu Val Thr Val Ser Ala
            115

<210> SEQ ID NO 4
<211> LENGTH: 107
<212> TYPE: PRT
<213> ORGANISM: Artificial Sequence
<220> FEATURE:
<223> OTHER INFORMATION: Synthetic

<400> SEQUENCE: 4

Asp Ile Val Met Thr Gln Ser His Lys Phe Met Ser Thr Ser Val Gly
  1               5                  10                  15

Asp Arg Val Ser Ile Thr Cys Lys Ala Ser Gln Asp Val Phe Thr Ala
                 20                  25                  30

Val Ala Trp Tyr Gln Gln Lys Pro Gly Gln Ser Pro Lys Leu Leu Ile
             35                  40                  45

Tyr Ser Ala Ser Tyr Arg Tyr Thr Gly Val Pro Asp Arg Phe Thr Gly
         50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Trp
                     85                  90                  95

Thr Phe Gly Gly Gly Thr Arg Leu Glu Ile Lys
                100                 105

<210> SEQ ID NO 5
<211> LENGTH: 119
<212> TYPE: PRT
<213> ORGANISM: Artificial Sequence
<220> FEATURE:
<223> OTHER INFORMATION: Synthetic

<400> SEQUENCE: 5

Glu Phe Gln Leu Gln Gln Ser Gly Pro Glu Leu Val Lys Pro Gly Ala
  1               5                  10                  15

Ser Val Lys Ile Ser Cys Arg Ala Ser Gly Tyr Ser Phe Thr Ala Tyr
                 20                  25                  30

Ser Met Asn Trp Val Gln Gln Thr Asn Gly Lys Ser Leu Glu Trp Ile
             35                  40                  45

Gly Val Ile Asn Pro Lys Phe Gly Thr Ile Asn Tyr Asn Gln Lys Phe
         50                  55                  60

Lys Gly Lys Ala Thr Leu Thr Val Asp Gln Ser Ser Ser Ala Ala Tyr
 65                  70                  75                  80

Ile Gln Leu Asn Ser Leu Thr Ser Glu Asp Ser Ala Val Tyr Phe Cys
                     85                  90                  95

Ala Arg Asn Gly Asn Phe Ala Trp Tyr Phe Asp Val Trp Gly Thr Gly
                100                 105                 110

Thr Thr Val Thr Val Ser Ser
            115
```

<210> SEQ ID NO 6
<211> LENGTH: 107
<212> TYPE: PRT
<213> ORGANISM: Artificial Sequence
<220> FEATURE:
<223> OTHER INFORMATION: Synthetic

<400> SEQUENCE: 6

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Phe Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Pro Glu Gly Val Pro Ser Arg Phe Ser Gly
    50                  55                  60

Ser Gly Ser Gly Thr Gln Phe Ser Leu Lys Ile Asn Ser Leu Gln Ser
65                  70                  75                  80

Glu Asp Phe Gly Ser Tyr Tyr Cys Gln His His Tyr Gly Val Pro Trp
                85                  90                  95

Thr Phe Gly Gly Gly Thr Lys Leu Glu Ile Lys
            100                 105

<210> SEQ ID NO 7
<211> LENGTH: 119
<212> TYPE: PRT
<213> ORGANISM: Artificial Sequence
<220> FEATURE:
<223> OTHER INFORMATION: Synthetic

<400> SEQUENCE: 7

Glu Phe Gln Leu Gln Gln Ser Gly Pro Glu Leu Val Lys Pro Gly Ala
1               5                   10                  15

Ser Val Lys Ile Ser Cys Arg Ala Ser Gly Tyr Ser Phe Thr Ala Tyr
            20                  25                  30

Ser Ile Asn Trp Val Gln Gln Thr Asn Gly Lys Ser Leu Glu Trp Ile
        35                  40                  45

Gly Val Ile Asn Pro Lys Phe Gly Thr Ile Asn Tyr Asn Gln Lys Phe
    50                  55                  60

Lys Gly Lys Ala Thr Leu Thr Val Asp Gln Ser Ser Ser Ala Ala Tyr
65                  70                  75                  80

Met Gln Leu Asn Ser Leu Thr Ser Glu Asp Ser Ala Val Tyr Phe Cys
                85                  90                  95

Ala Arg Asn Gly Asn Phe Ala Trp Tyr Phe Asp Val Trp Gly Thr Gly
            100                 105                 110

Thr Thr Val Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Synthetic

<400> SEQUENCE: 8

Asp Ile Gln Met Thr Gln Ser Pro Ala Ser Leu Ser Ala Ser Val Gly
1               5                   10                  15

Glu Thr Val Thr Ile Thr Cys Arg Ala Gly Glu Asn Ile Tyr Ser Tyr

```
                    20                  25                  30
Leu Ala Trp Tyr Gln Gln Lys Gln Gly Lys Ser Pro Gln Leu Leu Val
            35                  40                  45

Tyr Asn Ala Lys Thr Leu Pro Glu Gly Val Pro Ser Arg Phe Ser Gly
        50                  55                  60

Ser Gly Ser Gly Thr Gln Phe Ser Leu Lys Ile Asn Ser Leu Gln Ser
65                  70                  75                  80

Glu Asp Phe Gly Ser Tyr Tyr Cys Gln His His Tyr Gly Val Pro Trp
                85                  90                  95

Thr Phe Gly Gly Gly Thr Lys Leu Glu Ile Lys
                100                 105

<210> SEQ ID NO 9
<211> LENGTH: 119
<212> TYPE: PRT
<213> ORGANISM: Artificial Sequence
<220> FEATURE:
<223> OTHER INFORMATION: Synthetic

<400> SEQUENCE: 9

Glu Phe Gln Leu Gln Gln Ser Gly Pro Glu Leu Val Lys Pro Gly Ala
1               5                   10                  15

Ser Val Lys Ile Ser Cys Arg Ala Ser Gly Tyr Ser Phe Thr Ala Tyr
            20                  25                  30

Ser Met Asn Trp Val Gln Gln Thr Asn Gly Lys Ser Leu Glu Trp Ile
        35                  40                  45

Gly Val Ile Asn Pro Lys Phe Gly Thr Thr Asn Tyr Asn Gln Lys Phe
    50                  55                  60

Arg Asp Lys Ala Thr Leu Thr Val Asp His Ser Ser Ala Ala Tyr
65                  70                  75                  80

Met Gln Leu Asn Ser Leu Thr Ser Glu Asp Ser Ala Val Tyr Phe Cys
                85                  90                  95

Ala Arg Asn Gly Asn Phe Ala Trp Tyr Phe Asp Val Trp Gly Thr Gly
                100                 105                 110

Thr Thr Val Thr Val Ser Ser
        115

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Phe Ser Tyr
            20                  25                  30

Leu Ala Trp Tyr Gln Gln Lys Gln Gly Lys Ser Pro Gln Leu Leu Ala
            35                  40                  45

Tyr Asn Ala Glu Thr Leu Ala Glu Gly Val Pro Ser Arg Phe Ser Gly
        50                  55                  60

Ser Gly Ser Gly Thr Gln Phe Ser Leu Lys Ile Ser Ser Leu Gln Ser
65                  70                  75                  80

Glu Asp Phe Gly Ser Tyr Tyr Cys Gln His His Phe Gly Val Pro Trp
                85                  90                  95
```

Thr Phe Gly Gly Gly Thr Asn Leu Glu Ile Lys
        100                 105

<210> SEQ ID NO 11
<211> LENGTH: 119
<212> TYPE: PRT
<213> ORGANISM: Artificial Sequence
<220> FEATURE:
<223> OTHER INFORMATION: Synthetic

<400> SEQUENCE: 11

Glu Val Gln Leu Val Glu Ser Gly Gly Leu Val Met Pro Gly Gly
1               5                   10                  15

Ser Leu Lys Leu Ser Cys Ala Ala Ser Gly Phe Thr Phe Ser Gly Phe
            20                  25                  30

Val Met Ser Trp Val Arg Gln Thr Pro Glu Lys Arg Leu Glu Trp Val
        35                  40                  45

Ala Thr Ile Asn Asp Ala Gly Thr Tyr Thr Tyr Tyr Ser Asp Asn Leu
    50                  55                  60

Lys Gly Arg Phe Thr Ile Ser Arg Asp Asn Ala Lys Asn Asn Leu Tyr
65                  70                  75                  80

Leu Gln Met Ser His Leu Lys Ser Glu Asp Ala Gly Met Tyr Tyr Cys
                85                  90                  95

Ala Arg Asp Gly Gly Leu Arg Ala Trp Phe Pro Tyr Trp Gly Pro Gly
            100                 105                 110

Thr Leu Val Thr Val Ser Ala
        115

<210> SEQ ID NO 12
<211> LENGTH: 107
<212> TYPE: PRT
<213> ORGANISM: Artificial Sequence
<220> FEATURE:
<223> OTHER INFORMATION: Synthetic

<400> SEQUENCE: 12

Asp Ile Gln Leu Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Leu Lys Gln Gly Lys Ser Pro Gln Leu Leu Val
        35                  40                  45

Phe Asn Thr Lys Thr Leu Ala Glu Gly Val Pro Ser Arg Phe Ser Gly
    50                  55                  60

Ser Gly Ser Gly Thr Gln Phe Ser Leu Arg Ile Asp Ser Leu Gln Leu
65                  70                  75                  80

Glu Asp Phe Gly Ser Phe Tyr Cys Gln His His Ile Gly Ser Pro Arg
                85                  90                  95

Thr Phe Gly Gly Gly Thr Thr Leu Glu Ile Arg
        100                 105

<210> SEQ ID NO 13
<211> LENGTH: 119
<212> TYPE: PRT
<213> ORGANISM: Artificial Sequence
<220> FEATURE:
<223> OTHER INFORMATION: Synthetic

<400> SEQUENCE: 13

Glu Phe Gln Leu Gln Gln Ser Gly Pro Glu Leu Val Lys Pro Gly Ala

```
1               5                   10                  15
Ser Val Lys Ile Ser Cys Arg Ala Ser Gly Tyr Ser Phe Thr Ala Tyr
                20                  25                  30

Ser Met Asn Trp Val Gln Gln Thr Asn Gly Lys Ser Leu Glu Trp Ile
            35                  40                  45

Gly Val Ile Asn Pro Lys Phe Gly Thr Ile Asn Tyr Asn Gln Lys Phe
        50                  55                  60

Lys Asp Lys Ala Thr Leu Thr Val Asp His Ser Ser Ala Ala Tyr
65                  70                  75                  80

Met Gln Leu Asn Ser Leu Thr Ser Glu Asp Ser Ala Val Tyr Phe Cys
                85                  90                  95

Ala Arg Asn Gly Asn Phe Ala Trp Tyr Phe Asp Val Trp Gly Thr Gly
                100                 105                 110

Thr Thr Val Thr Val Ser Ser
            115
```

<210> SEQ ID NO 14
<211> LENGTH: 107
<212> TYPE: PRT
<213> ORGANISM: Artificial Sequence
<220> FEATURE:
<223> OTHER INFORMATION: Synthetic

<400> SEQUENCE: 14

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Ser Ile Phe Ser Tyr
                20                  25                  30

Leu Ala Trp Tyr Gln Gln Lys Gln Gly Lys Ser Pro Gln Leu Leu Ala
            35                  40                  45

Tyr Asn Ala Glu Thr Leu Ala Glu Gly Val Pro Ser Arg Phe Ser Gly
        50                  55                  60

Ser Gly Ser Gly Thr Gln Phe Ser Leu Lys Ile Asn Ser Leu Gln Ser
65                  70                  75                  80

Glu Asp Phe Gly Ile Tyr Tyr Cys Gln His His Phe Gly Val Pro Trp
                85                  90                  95

Thr Phe Gly Gly Gly Thr Lys Leu Glu Ile Lys
            100                 105
```

<210> SEQ ID NO 15
<211> LENGTH: 119
<212> TYPE: PRT
<213> ORGANISM: Artificial Sequence
<220> FEATURE:
<223> OTHER INFORMATION: Synthetic

<400> SEQUENCE: 15

```
Glu Ile Gln Leu Gln Gln Thr Gly Pro Glu Leu Val Lys Pro Gly Ala
1               5                   10                  15

Ser Val Asn Ile Ser Cys Lys Ala Ser Gly Tyr Ser Phe Thr Asp Tyr
                20                  25                  30

Ile Met Ile Trp Val Lys Gln Ser His Gly Lys Ser Leu Glu Trp Ile
            35                  40                  45

Gly Asn Ile His Pro Tyr Phe Gly Asn Ser His Tyr Asn Leu Lys Phe
        50                  55                  60

Lys Gly Lys Ala Thr Leu Thr Val Asp Lys Ser Ser Thr Thr Ala Tyr
65                  70                  75                  80
```

```
Met Gln Leu Asn Ser Leu Thr Ser Glu Asp Ser Ala Val Tyr Tyr Cys
                85                  90                  95

Ala Arg Arg Gly Ile Thr Ser Ala His Phe Asp Tyr Trp Gly Gln Gly
            100                 105                 110

Thr Thr Leu Thr Val Ser Ser
        115

<210> SEQ ID NO 16
<211> LENGTH: 111
<212> TYPE: PRT
<213> ORGANISM: Artificial Sequence
<220> FEATURE:
<223> OTHER INFORMATION: Synthetic

<400> SEQUENCE: 16

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Gly
                85                  90                  95

Asp Leu Pro Trp Thr Phe Gly Gly Gly Thr Lys Leu Glu Ile Lys
            100                 105                 110

<210> SEQ ID NO 17
<211> LENGTH: 115
<212> TYPE: PRT
<213> ORGANISM: Artificial Sequence
<220> FEATURE:
<223> OTHER INFORMATION: Synthetic

<400> SEQUENCE: 17

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Ser Asp Tyr
            20                  25                  30

Thr Leu His Trp Val Lys Gln Ser His Gly Lys Asn Leu Glu Trp Ile
        35                  40                  45

Gly Gly Phe Asn Pro Asn Asn Gly Gly Thr Asn Tyr Asn Gln Lys Phe
    50                  55                  60

Lys Val Lys Ala Ser Leu Thr Ile Asp Lys Ser Asn Ser Thr Val Tyr
65                  70                  75                  80

Met Glu Leu Arg Ser Leu Ser Ser Glu Asp Ser Ala Val Tyr Tyr Cys
                85                  90                  95

Ala Arg Asn Trp Ala Phe Asp Tyr Trp Gly Gln Gly Thr Thr Leu Thr
            100                 105                 110

Val Ser Ser
        115

<210> SEQ ID NO 18
<211> LENGTH: 107
<212> TYPE: PRT
<213> ORGANISM: Artificial Sequence
```

<220> FEATURE:
<223> OTHER INFORMATION: Synthetic

<400> SEQUENCE: 18

Asp Ile Val Met Thr Gln Ser His Lys Ile Met Ser Thr Ser Leu Gly
1               5                   10                  15

Asp Arg Val Asn Ile Thr Cys Lys Ala Ser Gln His Val Ser Thr Ala
            20                  25                  30

Val Ala Trp Tyr Gln Gln Arg Pro Gly Gln Ser Pro Arg Leu Leu Ile
        35                  40                  45

Tyr Ser Ala Ser Tyr Arg His Thr Gly Val Pro Asp Arg Phe Thr Gly
50                  55                  60

Ser Gly Ser Gly Thr Asp Ile Thr Phe Thr Ile Ser Ser Val Gln Thr
65                  70                  75                  80

Glu Asp Leu Ala Val Tyr Tyr Cys Gln Gln Tyr Tyr Thr Thr Pro Trp
                85                  90                  95

Thr Phe Gly Gly Gly Thr Lys Leu Glu Ile Lys
            100                 105

<210> SEQ ID NO 19
<211> LENGTH: 115
<212> TYPE: PRT
<213> ORGANISM: Artificial Sequence
<220> FEATURE:
<223> OTHER INFORMATION: Synthetic

<400> SEQUENCE: 19

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Ala Tyr
            20                  25                  30

Gly Met Ser Trp Val Lys Gln Thr Pro Gly Lys Gly Leu Lys Trp Met
        35                  40                  45

Gly Trp Ile Asn Thr Tyr Ser Gly Val Pro Thr Tyr Ala Asp Asp Phe
50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Thr Arg Gly Asp Thr Gly Gly Tyr Trp Gly Gln Gly Ala Thr Leu Thr
            100                 105                 110

Val Ser Ser
        115

<210> SEQ ID NO 20
<211> LENGTH: 105
<212> TYPE: PRT
<213> ORGANISM: Artificial Sequence
<220> FEATURE:
<223> OTHER INFORMATION: Synthetic

<400> SEQUENCE: 20

Gln Ile Val Leu Thr Gln Ser Pro Ala Ile Met Ser Ala Ser Leu Gly
1               5                   10                  15

Glu Glu Ile Thr Leu Thr Cys Ser Ala Arg Ser Ser Val Ser Asp Met
            20                  25                  30

His Trp Tyr Gln Gln Lys Ser Gly Thr Ser Pro Lys Leu Leu Ile Tyr
        35                  40                  45

```
Ser Thr Ser Asn Leu Ala Ser Gly Val Pro Ser Arg Phe Ser Gly Ser
     50                  55                  60

Gly Ser Gly Thr Phe Phe Ser Leu Thr Ile Ser Ser Val Glu Ala Glu
 65                  70                  75                  80

Asp Ala Ala Asp Tyr Tyr Cys His Gln Trp Gly Tyr Pro Thr Phe
                 85                  90                  95

Gly Gly Gly Thr Lys Leu Glu Ile Lys
             100                 105
```

<210> SEQ ID NO 21
<211> LENGTH: 119
<212> TYPE: PRT
<213> ORGANISM: Artificial Sequence
<220> FEATURE:
<223> OTHER INFORMATION: Synthetic

<400> SEQUENCE: 21

```
Gln Ile Gln Leu Val Gln Ser Gly Pro Glu Leu Lys Lys Pro Gly Glu
 1                5                  10                  15

Thr Val Lys Ile Ser Cys Lys Ala Ser Gly Tyr Thr Phe Thr Ala Tyr
                 20                  25                  30

Gly Met Gly Trp Val Lys Gln Ala Pro Gly Lys Gly Leu Lys Trp Met
             35                  40                  45

Gly Trp Ile Asn Thr Tyr Ser Gly Val Pro Thr Tyr Ala Asp Asp Phe
 50                  55                  60

Lys Gly Arg Phe Ala Phe Ser Leu Glu Ser Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Gly Ile Tyr Phe Gly Asn Tyr Phe Asp Tyr Trp Gly Gln Gly
             100                 105                 110

Thr Thr Leu Thr Val Ser Ser
            115
```

<210> SEQ ID NO 22
<211> LENGTH: 107
<212> TYPE: PRT
<213> ORGANISM: Artificial Sequence
<220> FEATURE:
<223> OTHER INFORMATION: Synthetic

<400> SEQUENCE: 22

```
Asp Ile Gln Met Thr Gln Ser Pro Ala Ser Leu Ser Ala Ser Val Gly
 1                5                  10                  15

Glu Thr Val Thr Ile Thr Cys Arg Ala Ser Glu Ile Ile Tyr Thr Phe
                 20                  25                  30

Leu Ala Trp Tyr Gln Gln Lys Gln Gly Lys Ser Pro Gln Leu Leu Val
             35                  40                  45

Tyr Asn Ala Asn Thr Leu Ala Glu Gly Val Pro Ser Arg Phe Ser Gly
 50                  55                  60

Ser Gly Ser Gly Thr Gln Phe Ser Leu Lys Ile Asn Ser Leu Gln Pro
 65                  70                  75                  80

Glu Asp Phe Gly Ser Tyr Tyr Cys Gln His His Tyr Gly Ser Pro Tyr
                 85                  90                  95

Thr Phe Gly Gly Gly Thr Thr Leu Glu Ile Lys
             100                 105
```

<210> SEQ ID NO 23

```
<211> LENGTH: 119
<212> TYPE: PRT
<213> ORGANISM: Artificial Sequence
<220> FEATURE:
<223> OTHER INFORMATION: Synthetic

<400> SEQUENCE: 23

Gln Ile Gln Leu Ile Gln Ser Gly Pro Glu Val Lys Pro Gly Glu
1               5                   10                  15

Thr Val Lys Ile Ser Cys Lys Ala Ser Gly Tyr Thr Phe Thr Thr Tyr
            20                  25                  30

Ala Met Thr Trp Val Lys Gln Ala Ala Gly Lys Gly Leu Lys Trp Met
        35                  40                  45

Gly Trp Ile His Thr Tyr Ser Gly Val Pro Thr Tyr Val Asp Asp Phe
    50                  55                  60

Lys Gly Arg Phe Ala Phe Ser Leu Asp Thr Ser Ala Asn Thr Ala Tyr
65                  70                  75                  80

Leu Gln Ile Asn Asn Leu Lys Asn Glu Asp Thr Ala Thr Tyr Phe Cys
                85                  90                  95

Ala Arg Tyr Asp Gly Pro Leu Tyr Ala Met Asp Phe Trp Gly Gln Gly
            100                 105                 110

Thr Ser Val Thr Val Ser Ser
        115

<210> SEQ ID NO 24
<211> LENGTH: 106
<212> TYPE: PRT
<213> ORGANISM: Artificial Sequence
<220> FEATURE:
<223> OTHER INFORMATION: Synthetic

<400> SEQUENCE: 24

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
            20                  25                  30

Phe Trp Tyr Gln Gln Lys Pro Gly Ser Ser Pro Lys Ser Trp Ile Tyr
        35                  40                  45

Arg Thr Ser Asn Leu Ala Ser Gly Val Pro Gly Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Phe Pro Thr
                85                  90                  95

Phe Gly Gly Gly Thr Lys Leu Glu Ile Lys
            100                 105

<210> SEQ ID NO 25
<211> LENGTH: 117
<212> TYPE: PRT
<213> ORGANISM: Artificial Sequence
<220> FEATURE:
<223> OTHER INFORMATION: Synthetic

<400> SEQUENCE: 25

Asp Val Gln Leu Gln Glu Ser Gly Pro Gly Met Val Lys Pro Ser Gln
1               5                   10                  15

Ser Leu Ser Leu Thr Cys Thr Val Thr Gly Tyr Ser Ile Thr Ser Gly
            20                  25                  30
```

Tyr Asp Trp His Trp Ile Arg His Phe Pro Gly Asn Lys Leu Glu Trp
            35                  40                  45

Met Gly Phe Ile Ser Asp Ser Gly Ser Thr Lys Tyr Asn Pro Ser Leu
 50                  55                  60

Lys Ser Arg Ile Ser Ile Thr His Asp Thr Ser Lys Asn His Phe Phe
 65                  70                  75                  80

Leu Lys Leu Asn Ser Val Thr Ser Glu Asp Thr Ala Thr Tyr Tyr Cys
                 85                  90                  95

Ala Arg Gly Ser Tyr Trp Tyr Phe Asp Val Trp Gly Thr Gly Thr Thr
            100                 105                 110

Val Thr Val Ser Ser
        115

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

Asp Ile Gln Met Thr Gln Ser Pro Ala Ser Leu Ser Ala Ser Val Gly
 1               5                  10                  15

Glu Thr Val Thr Ile Thr Cys Arg Ala Ser Glu Asn Ile Tyr Ser Tyr
             20                  25                  30

Leu Ala Trp Tyr Gln Gln Lys Gln Gly Lys Ser Pro Gln Leu Leu Val
         35                  40                  45

Asn Asn Ala Lys Thr Leu Ala Glu Gly Val Ser Ser Arg Phe Ser Gly
 50                  55                  60

Ser Gly Ser Gly Thr Gln Phe Ser Leu Lys Ile Asn Ser Leu Gln Pro
 65                  70                  75                  80

Glu Asp Phe Gly Ser Tyr Tyr Cys Gln His His Tyr Gly Asn Pro Leu
                 85                  90                  95

Met Phe Gly Ala Gly Thr Lys Leu Glu Leu Lys
            100                 105

<210> SEQ ID NO 27
<211> LENGTH: 119
<212> TYPE: PRT
<213> ORGANISM: Artificial Sequence
<220> FEATURE:
<223> OTHER INFORMATION: Synthetic

<400> SEQUENCE: 27

Glu Val Lys Leu Val Glu Ser Gly Gly Ala Leu Val Gln Pro Gly Gly
 1               5                  10                  15

Ser Leu Lys Leu Ser Cys Ala Ala Ser Gly Phe Thr Phe Ser Asp Tyr
             20                  25                  30

Tyr Met Tyr Trp Val Arg Gln Thr Pro Glu Lys Arg Leu Glu Trp Val
         35                  40                  45

Ala Ser Ile Thr Lys Gly Gly Gly Ser Thr Tyr Tyr Pro Asp Thr Leu
 50                  55                  60

Lys Gly Arg Phe Thr Ile Ser Arg Asp Asn Ala Lys Asn Thr Leu Tyr
 65                  70                  75                  80

Leu Gln Met Ser Arg Leu Lys Ser Glu Asp Thr Asp Met Tyr Tyr Cys
                 85                  90                  95

Ala Arg Gln Ser Ser Tyr Asp Phe Val Met Asp Tyr Trp Gly Gln Gly
            100                 105                 110

Thr Ser Val Thr Val Ser Ser
        115

<210> SEQ ID NO 28
<211> LENGTH: 107
<212> TYPE: PRT
<213> ORGANISM: Artificial Sequence
<220> FEATURE:
<223> OTHER INFORMATION: Synthetic

<400> SEQUENCE: 28

Asp Ile Val Met Thr Gln Ser His Lys Phe Met Ser Thr Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Gln Ser Pro Lys Leu Leu Ile
        35                  40                  45

Tyr Trp Ala Ser Ala Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Asn Tyr Pro Leu
                85                  90                  95

Thr Phe Gly Val Gly Thr Lys Leu Glu Leu Lys
            100                 105

<210> SEQ ID NO 29
<211> LENGTH: 5
<212> TYPE: PRT
<213> ORGANISM: Artificial Sequence
<220> FEATURE:
<223> OTHER INFORMATION: Synthetic

<400> SEQUENCE: 29

Glu Asn Thr Met His
1               5

<210> SEQ ID NO 30
<211> LENGTH: 17
<212> TYPE: PRT
<213> ORGANISM: Artificial Sequence
<220> FEATURE:
<223> OTHER INFORMATION: Synthetic

<400> SEQUENCE: 30

Gly Ile Asn Pro Asn Gln Gly Gly Asn Arg Asn Asn Gln Lys Phe Lys
1               5                   10                  15

Gly

<210> SEQ ID NO 31
<211> LENGTH: 10
<212> TYPE: PRT
<213> ORGANISM: Artificial Sequence
<220> FEATURE:
<223> OTHER INFORMATION: Synthetic

<400> SEQUENCE: 31

Ser Gly Leu Arg Asp Tyr Ala Met Asp Tyr
1               5                   10

<210> SEQ ID NO 32
<211> LENGTH: 11

```
<212> TYPE: PRT
<213> ORGANISM: Artificial Sequence
<220> FEATURE:
<223> OTHER INFORMATION: Synthetic

<400> SEQUENCE: 32

Lys Ala Ser Gln His Val Ser Thr Ala Val Val
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Synthetic

<400> SEQUENCE: 33

Ser Pro Ser Tyr Arg Tyr Thr
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic

<400> SEQUENCE: 34

Gln Gln His Tyr Ser Thr Pro Trp Thr
1               5

<210> SEQ ID NO 35
<211> LENGTH: 119
<212> TYPE: PRT
<213> ORGANISM: Artificial Sequence
<220> FEATURE:
<223> OTHER INFORMATION: Synthetic

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Asn
            20                  25                  30

Thr Met His Trp Val Arg Gln Ala Pro Gly Gln Arg Leu Glu Trp Met
        35                  40                  45

Gly Gly Ile Asn Pro Asn Gln Gly Asn Arg Asn Asn Gln Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Leu Arg Asp Tyr Ala Met Asp Tyr Trp Gly Gln Gly
            100                 105                 110

Thr Leu Val Thr Val Ser Ser
        115

<210> SEQ ID NO 36
<211> LENGTH: 119
<212> TYPE: PRT
<213> ORGANISM: Artificial Sequence
<220> FEATURE:
<223> OTHER INFORMATION: Synthetic

<400> SEQUENCE: 36
```

Gln Val Gln Leu Val Gln Ser Gly Ala Glu Val Val Lys Pro Gly Ala
1               5                   10                  15

Ser Val Lys Val Ser Cys Lys Thr Ser Gly Tyr Thr Phe Thr Glu Asn
            20                  25                  30

Thr Met His Trp Val Arg Gln Ala Pro Gly Gln Arg Leu Glu Trp Met
        35                  40                  45

Gly Gly Ile Asn Pro Gln Asn Gly Asn Arg Asn Asn Gln Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Gly Leu Arg Asp Tyr Ala Met Asp Tyr Trp Gly Gln Gly
            100                 105                 110

Thr Leu Val Thr Val Ser Ser
        115

<210> SEQ ID NO 37
<211> LENGTH: 119
<212> TYPE: PRT
<213> ORGANISM: Artificial Sequence
<220> FEATURE:
<223> OTHER INFORMATION: Synthetic

<400> SEQUENCE: 37

Gln Val Gln Leu Val Gln Ser Gly Ala Glu Val Val Lys Pro Gly Ala
1               5                   10                  15

Ser Val Lys Val Ser Cys Lys Thr Ser Gly Tyr Thr Phe Thr Glu Asn
            20                  25                  30

Thr Met His Trp Val Lys Gln Ala Pro Gly Gln Arg Leu Glu Trp Ile
        35                  40                  45

Gly Gly Ile Asn Pro Asn Gln Gly Gly Asn Arg Asn Asn Gln Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Ser Ala Val Tyr Tyr Cys
            85                  90                  95

Ala Arg Ser Gly Leu Arg Asp Tyr Ala Met Asp Tyr Trp Gly Gln Gly
            100                 105                 110

Thr Leu Val Thr Val Ser Ser
        115

<210> SEQ ID NO 38
<211> LENGTH: 119
<212> TYPE: PRT
<213> ORGANISM: Artificial Sequence
<220> FEATURE:
<223> OTHER INFORMATION: Synthetic

<400> SEQUENCE: 38

Gln Val Gln Leu Val Gln Ser Gly Ala Glu Val Val Lys Pro Gly Ala
1               5                   10                  15

Ser Val Lys Ile Ser Cys Lys Thr Ser Gly Tyr Thr Phe Thr Glu Asn
            20                  25                  30

Thr Met His Trp Val Lys Gln Ala Pro Gly Gln Arg Leu Glu Trp Ile
        35                  40                  45

Gly Gly Ile Asn Pro Asn Gln Gly Gly Asn Arg Asn Asn Gln Lys Phe

```
                50                  55                  60
Lys Gly Arg Ala Thr Leu Thr Val Asp Thr Ser Ala Ser Thr Ala Tyr
 65                  70                  75                  80

Met Glu Leu Ser Ser Leu Arg Ser Glu Asp Ser Ala Val Tyr Tyr Cys
                 85                  90                  95

Ala Arg Ser Gly Leu Arg Asp Tyr Ala Met Asp Tyr Trp Gly Gln Gly
                100                 105                 110

Thr Leu Val Thr Val Ser Ser
            115

<210> SEQ ID NO 39
<211> LENGTH: 107
<212> TYPE: PRT
<213> ORGANISM: Artificial Sequence
<220> FEATURE:
<223> OTHER INFORMATION: Synthetic

<400> SEQUENCE: 39

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln His Val Ser Thr Ala
                 20                  25                  30

Val Val Trp Tyr Gln Gln Lys Pro Gly Lys Ala Pro Lys Leu Leu Ile
             35                  40                  45

Tyr Ser Pro Ser Tyr Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Ser Thr Pro Trp
                 85                  90                  95

Thr Phe Gly Gln Gly Thr Lys Val Glu Ile Lys
                100                 105

<210> SEQ ID NO 40
<211> LENGTH: 107
<212> TYPE: PRT
<213> ORGANISM: Artificial Sequence
<220> FEATURE:
<223> OTHER INFORMATION: Synthetic

<400> SEQUENCE: 40

Asp Ile Gln Met Thr Gln Ser Pro Ser Ser Leu Ser Thr Ser Val Gly
  1               5                  10                  15

Asp Arg Val Thr Ile Thr Cys Lys Ala Ser Gln His Val Ser Thr Ala
                 20                  25                  30

Val Val Trp Tyr Gln Gln Lys Pro Gly Lys Ala Pro Lys Leu Leu Ile
             35                  40                  45

Tyr Ser Pro Ser Tyr Arg Tyr Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Gln Gln His Tyr Ser Thr Pro Trp
                 85                  90                  95

Thr Phe Gly Gln Gly Thr Lys Val Glu Ile Lys
                100                 105

<210> SEQ ID NO 41
<211> LENGTH: 107
```

<212> TYPE: PRT
<213> ORGANISM: Artificial Sequence
<220> FEATURE:
<223> OTHER INFORMATION: Synthetic

<400> SEQUENCE: 41

Asp Ile Gln Met Thr Gln Ser Pro Ser Ser Leu Ser Thr Ser Val Gly
1               5                   10                  15

Asp Arg Val Thr Ile Thr Cys Lys Ala Ser Gln His Val Ser Thr Ala
            20                  25                  30

Val Val Trp Tyr Gln Gln Lys Pro Gly Lys Ala Pro Lys Leu Leu Ile
        35                  40                  45

Tyr Ser Pro Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Val Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Val Glu Ile Lys
            100                 105

<210> SEQ ID NO 42
<211> LENGTH: 107
<212> TYPE: PRT
<213> ORGANISM: Artificial Sequence
<220> FEATURE:
<223> OTHER INFORMATION: Synthetic

<400> SEQUENCE: 42

Asp Ile Gln Met Thr Gln Ser Pro Ser Ser Leu Ser Thr Ser Val Gly
1               5                   10                  15

Asp Arg Val Thr Ile Thr Cys Lys Ala Ser Gln His Val Ser Thr Ala
            20                  25                  30

Val Val Trp Tyr Gln Gln Lys Pro Gly Lys Ala Pro Lys Leu Leu Ile
        35                  40                  45

Tyr Ser Pro Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Val Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Leu Glu Ile Lys
            100                 105

<210> SEQ ID NO 43
<211> LENGTH: 5
<212> TYPE: PRT
<213> ORGANISM: Artificial Sequence
<220> FEATURE:
<223> OTHER INFORMATION: Synthetic

<400> SEQUENCE: 43

Asp Tyr Tyr Met Tyr
1               5

<210> SEQ ID NO 44
<211> LENGTH: 17
<212> TYPE: PRT
<213> ORGANISM: Artificial Sequence
<220> FEATURE:
<223> OTHER INFORMATION: Synthetic

```
<400> SEQUENCE: 44

Ser Ile Thr Lys Gly Gly Gly Ser Thr Tyr Tyr Pro Asp Thr Leu Lys
1               5                   10                  15

Gly

<210> SEQ ID NO 45
<211> LENGTH: 10
<212> TYPE: PRT
<213> ORGANISM: Artificial Sequence
<220> FEATURE:
<223> OTHER INFORMATION: Synthetic

<400> SEQUENCE: 45

Gln Ser Ser Tyr Asp Phe Val Met Asp Tyr
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic

<400> SEQUENCE: 46

Lys Ala Ser Gln Asp Val Asp Thr Ala Val Ala
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Synthetic

<400> SEQUENCE: 47

Trp Ala Ser Ala Arg His Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gln Gln Tyr Ser Asn Tyr Pro Leu Thr
1               5

<210> SEQ ID NO 49
<211> LENGTH: 119
<212> TYPE: PRT
<213> ORGANISM: Artificial Sequence
<220> FEATURE:
<223> OTHER INFORMATION: Synthetic

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45
```

```
Ala Ser Ile Thr Lys Gly Gly Gly Ser Thr Tyr Tyr Pro Asp Thr Leu
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Ser Ser Tyr Asp Phe Val Met Asp Tyr Trp Gly Gln Gly
                100                 105                 110

Thr Thr Val Thr Val Ser Ser
            115

<210> SEQ ID NO 50
<211> LENGTH: 119
<212> TYPE: PRT
<213> ORGANISM: Artificial Sequence
<220> FEATURE:
<223> OTHER INFORMATION: Synthetic

<400> SEQUENCE: 50

Glu Val Lys Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                 20                  25                  30

Tyr Met Tyr Trp Val Arg Gln Ala Pro Gly Lys Gly Leu Glu Trp Val
             35                  40                  45

Ala Ser Ile Thr Lys Gly Gly Gly Ser Thr Tyr Tyr Pro Asp Thr Leu
         50                  55                  60

Lys Gly Arg Phe Thr Ile Ser Arg Asp Asn Ala Lys Asn Ser Leu Tyr
 65                  70                  75                  80

Leu Gln Met Asn Arg Leu Arg Ala Glu Asp Thr Ala Val Tyr Tyr Cys
                 85                  90                  95

Ala Arg Gln Ser Ser Tyr Asp Phe Val Met Asp Tyr Trp Gly Gln Gly
                100                 105                 110

Thr Thr Val Thr Val Ser Ser
            115

<210> SEQ ID NO 51
<211> LENGTH: 119
<212> TYPE: PRT
<213> ORGANISM: Artificial Sequence
<220> FEATURE:
<223> OTHER INFORMATION: Synthetic

<400> SEQUENCE: 51

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                 20                  25                  30

Tyr Met Tyr Trp Val Arg Gln Ala Pro Gly Lys Arg Leu Glu Trp Val
             35                  40                  45

Ala Ser Ile Thr Lys Gly Gly Gly Ser Thr Tyr Tyr Pro Asp Thr Leu
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Ser Ser Tyr Asp Phe Val Met Asp Tyr Trp Gly Gln Gly
                100                 105                 110
```

Thr Thr Val Thr Val Ser Ser
        115

<210> SEQ ID NO 52
<211> LENGTH: 119
<212> TYPE: PRT
<213> ORGANISM: Artificial Sequence
<220> FEATURE:
<223> OTHER INFORMATION: Synthetic

<400> SEQUENCE: 52

Glu Val Lys Leu Val Glu Ser Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Arg Leu Glu Trp Val
        35                  40                  45

Ala Ser Ile Thr Lys Gly Gly Ser Thr Tyr Tyr Pro Asp Thr Leu
    50                  55                  60

Lys Gly Arg Phe Thr Ile Ser Arg Asp Asn Ala Lys Asn Ser Leu Tyr
65              70                  75                  80

Leu Gln Met Asn Arg Leu Arg Ala Glu Asp Thr Ala Val Tyr Tyr Cys
                85                  90                  95

Ala Arg Gln Ser Ser Tyr Asp Phe Val Met Asp Tyr Trp Gly Gln Gly
            100                 105                 110

Thr Thr Val Thr Val Ser Ser
        115

<210> SEQ ID NO 53
<211> LENGTH: 107
<212> TYPE: PRT
<213> ORGANISM: Artificial Sequence
<220> FEATURE:
<223> OTHER INFORMATION: Synthetic

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Ala Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65              70                  75                  80

Glu Asp Ile Ala Thr Tyr Tyr Cys Gln Gln Tyr Ser Asn Tyr Pro Leu
                85                  90                  95

Thr Phe Gly Gln Gly Thr Lys Leu Glu Ile Lys
            100                 105

<210> SEQ ID NO 54
<211> LENGTH: 107
<212> TYPE: PRT
<213> ORGANISM: Artificial Sequence
<220> FEATURE:
<223> OTHER INFORMATION: Synthetic

<400> SEQUENCE: 54

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Ala Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Ser Asn Tyr Pro Leu
                85                  90                  95

Thr Phe Gly Gln Gly Thr Lys Leu Glu Ile Lys
            100                 105

<210> SEQ ID NO 55
<211> LENGTH: 107
<212> TYPE: PRT
<213> ORGANISM: Artificial Sequence
<220> FEATURE:
<223> OTHER INFORMATION: Synthetic

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Gln Ser Pro Lys Leu Leu Ile
        35                  40                  45

Tyr Trp Ala Ser Ala Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Tyr Ser Asn Tyr Pro Leu
                85                  90                  95

Thr Phe Gly Gln Gly Thr Lys Leu Glu Ile Lys
            100                 105

<210> SEQ ID NO 56
<211> LENGTH: 107
<212> TYPE: PRT
<213> ORGANISM: Artificial Sequence
<220> FEATURE:
<223> OTHER INFORMATION: Synthetic

<400> SEQUENCE: 56

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Gln Ser Pro Lys Leu Leu Ile
        35                  40                  45

Tyr Trp Ala Ser Ala Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Tyr Ser Asn Tyr Pro Leu
                85                  90                  95

Thr Phe Gly Gln Gly Thr Lys Leu Glu Ile Lys
            100                 105

<210> SEQ ID NO 57
<211> LENGTH: 6
<212> TYPE: PRT
<213> ORGANISM: Artificial Sequence
<220> FEATURE:
<223> OTHER INFORMATION: Synthetic

<400> SEQUENCE: 57

Ser Asp Tyr Ala Trp Asn
1               5

<210> SEQ ID NO 58
<211> LENGTH: 16
<212> TYPE: PRT
<213> ORGANISM: Artificial Sequence
<220> FEATURE:
<223> OTHER INFORMATION: Synthetic

<400> SEQUENCE: 58

Tyr Ile Ser Tyr Ser Gly Asn Thr Arg Tyr Asn Pro Ser Leu Lys Ser
1               5                   10                  15

<210> SEQ ID NO 59
<211> LENGTH: 9
<212> TYPE: PRT
<213> ORGANISM: Artificial Sequence
<220> FEATURE:
<223> OTHER INFORMATION: Synthetic

<400> SEQUENCE: 59

Lys Tyr Tyr Gly Ser Trp Phe Pro Tyr
1               5

<210> SEQ ID NO 60
<211> LENGTH: 11
<212> TYPE: PRT
<213> ORGANISM: Artificial Sequence
<220> FEATURE:
<223> OTHER INFORMATION: Synthetic

<400> SEQUENCE: 60

Lys Ala Ser Gln Asp Val Phe Thr Ala Val Ala
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Synthetic

<400> SEQUENCE: 61

Ser Ala Ser Tyr Arg Tyr Thr
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic

<400> SEQUENCE: 62

Gln Gln His Tyr Ser Thr Pro Trp Thr
1               5

<210> SEQ ID NO 63
<211> LENGTH: 118
<212> TYPE: PRT
<213> ORGANISM: Artificial Sequence
<220> FEATURE:
<223> OTHER INFORMATION: Synthetic

<400> SEQUENCE: 63

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Asn Thr Arg Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Lys Tyr Tyr Gly Ser Trp Phe Pro Tyr Trp Gly Gln Gly Thr
                100                 105                 110

Leu Val Thr Val Ser Ser
        115

<210> SEQ ID NO 64
<211> LENGTH: 118
<212> TYPE: PRT
<213> ORGANISM: Artificial Sequence
<220> FEATURE:
<223> OTHER INFORMATION: Synthetic

<400> SEQUENCE: 64

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Met Gly Tyr Ile Ser Tyr Ser Gly Asn Thr Arg Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Lys Tyr Tyr Gly Ser Trp Phe Pro Tyr Trp Gly Gln Gly Thr
                100                 105                 110

Leu Val Thr Val Ser Ser
        115

<210> SEQ ID NO 65
<211> LENGTH: 118
<212> TYPE: PRT
<213> ORGANISM: Artificial Sequence
<220> FEATURE:
<223> OTHER INFORMATION: Synthetic

```
<400> SEQUENCE: 65

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Asn Thr Arg Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Phe Ser Ser Val Thr Ala Ala Asp Thr Ala Val Tyr Tyr Cys
                85                  90                  95

Ser Arg Lys Tyr Tyr Gly Ser Trp Phe Pro Tyr Trp Gly Gln Gly Thr
                100                 105                 110

Leu Val Thr Val Ser Ser
        115

<210> SEQ ID NO 66
<211> LENGTH: 118
<212> TYPE: PRT
<213> ORGANISM: Artificial Sequence
<220> FEATURE:
<223> OTHER INFORMATION: Synthetic

<400> SEQUENCE: 66

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Met Gly Tyr Ile Ser Tyr Ser Gly Asn Thr Arg Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Phe Ser Ser Val Thr Ala Ala Asp Thr Ala Val Tyr Tyr Cys
                85                  90                  95

Ser Arg Lys Tyr Tyr Gly Ser Trp Phe Pro Tyr Trp Gly Gln Gly Thr
                100                 105                 110

Leu Val Thr Val Ser Ser
        115

<210> SEQ ID NO 67
<211> LENGTH: 107
<212> TYPE: PRT
<213> ORGANISM: Artificial Sequence
<220> FEATURE:
<223> OTHER INFORMATION: Synthetic

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Phe Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Arg Leu Glu Ile Lys
                100                 105

<210> SEQ ID NO 68
<211> LENGTH: 107
<212> TYPE: PRT
<213> ORGANISM: Artificial Sequence
<220> FEATURE:
<223> OTHER INFORMATION: Synthetic

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Phe Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Arg Leu Glu Ile Lys
                100                 105

<210> SEQ ID NO 69
<211> LENGTH: 107
<212> TYPE: PRT
<213> ORGANISM: Artificial Sequence
<220> FEATURE:
<223> OTHER INFORMATION: Synthetic

<400> SEQUENCE: 69

Asp Ile Gln Met Thr Gln Ser Pro Ser Ser Leu Ser Thr Ser Val Gly
1               5                   10                  15

Asp Arg Val Thr Ile Thr Cys Lys Ala Ser Gln Asp Val Phe Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Arg Leu Glu Ile Lys
                100                 105

<210> SEQ ID NO 70
<211> LENGTH: 107
<212> TYPE: PRT
<213> ORGANISM: Artificial Sequence
```

-continued

<220> FEATURE:
<223> OTHER INFORMATION: Synthetic

<400> SEQUENCE: 70

Asp Ile Gln Met Thr Gln Ser Pro Ser Ser Leu Ser Thr Ser Val Gly
1               5                   10                  15

Asp Arg Val Thr Ile Thr Cys Lys Ala Ser Gln Asp Val Phe Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Val Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Arg Leu Glu Ile Lys
            100                 105

<210> SEQ ID NO 71
<211> LENGTH: 118
<212> TYPE: PRT
<213> ORGANISM: Artificial Sequence
<220> FEATURE:
<223> OTHER INFORMATION: Synthetic

<400> SEQUENCE: 71

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Asp Asp
            20                  25                  30

Tyr Ala Trp Asn Trp Ile Arg Gln Pro Pro Gly Lys Gly Leu Glu Trp
        35                  40                  45

Met Gly Tyr Ile Ser Tyr Ser Gly His Thr Lys Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Lys Tyr Tyr Gly Gly Trp Phe Pro Arg Trp Gly Gln Gly Thr
            100                 105                 110

Leu Val Thr Val Ser Ser
        115

<210> SEQ ID NO 72
<211> LENGTH: 118
<212> TYPE: PRT
<213> ORGANISM: Artificial Sequence
<220> FEATURE:
<223> OTHER INFORMATION: Synthetic

<400> SEQUENCE: 72

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Asp Asp
            20                  25                  30

Tyr Ala Trp Asn Trp Ile Arg Gln Pro Pro Gly Lys Gly Leu Glu Trp
        35                  40                  45

```
Met Gly Tyr Ile Ser Tyr Ser Gly Asn Thr Met Tyr Asn Pro Ser Leu
        50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Lys Tyr Tyr Gly Gly Trp Phe Pro Ile Trp Gly Gln Gly Thr
                100                 105                 110

Leu Val Thr Val Ser Ser
            115

<210> SEQ ID NO 73
<211> LENGTH: 118
<212> TYPE: PRT
<213> ORGANISM: Artificial Sequence
<220> FEATURE:
<223> OTHER INFORMATION: Synthetic

<400> SEQUENCE: 73

Gln Val Gln Leu Gln Glu Ser Gly Pro Gly Leu Val Lys Pro Ser Gln
 1               5                   10                  15

Thr Leu Ser Leu Thr Cys Thr Val Ser Gly Tyr Ser Ile Thr Asp Asp
                20                  25                  30

Tyr Ala Trp Asn Trp Ile Arg Gln Pro Pro Gly Lys Gly Leu Glu Trp
                35                  40                  45

Met Gly Tyr Ile Ser Tyr Ser Gly Asp Thr Lys Tyr Asn Pro Ser Leu
        50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Lys Tyr Tyr Gly Gly Trp Phe Pro Val Trp Gly Gln Gly Thr
                100                 105                 110

Leu Val Thr Val Ser Ser
            115

<210> SEQ ID NO 74
<211> LENGTH: 118
<212> TYPE: PRT
<213> ORGANISM: Artificial Sequence
<220> FEATURE:
<223> OTHER INFORMATION: Synthetic

<400> SEQUENCE: 74

Gln Val Gln Leu Gln Glu Ser Gly Pro Gly Leu Val Lys Pro Ser Gln
 1               5                   10                  15

Thr Leu Ser Leu Thr Cys Thr Val Ser Gly Tyr Ser Ile Thr Asp Asp
                20                  25                  30

Tyr Ala Trp Asn Trp Ile Arg Gln Pro Pro Gly Lys Gly Leu Glu Trp
                35                  40                  45

Met Gly Tyr Ile Ser Tyr Ser Gly His Thr Arg Tyr Asn Pro Ser Leu
        50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Lys Tyr Tyr Gly Ser Trp Phe Pro Asp Trp Gly Gln Gly Thr
                100                 105                 110
```

```
Leu Val Thr Val Ser Ser
        115

<210> SEQ ID NO 75
<211> LENGTH: 118
<212> TYPE: PRT
<213> ORGANISM: Artificial Sequence
<220> FEATURE:
<223> OTHER INFORMATION: Synthetic

<400> SEQUENCE: 75

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Asp Asp
            20                  25                  30

Tyr Ala Trp Asn Trp Ile Arg Gln Pro Pro Gly Lys Gly Leu Glu Trp
        35                  40                  45

Met Gly Tyr Ile Ser Tyr Ser Gly Ile Thr Arg Tyr Asn Pro Ser Leu
50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Lys Tyr Tyr Gly Gly Trp Phe Pro Gln Trp Gly Gln Gly Thr
            100                 105                 110

Leu Val Thr Val Ser Ser
        115

<210> SEQ ID NO 76
<211> LENGTH: 107
<212> TYPE: PRT
<213> ORGANISM: Artificial Sequence
<220> FEATURE:
<223> OTHER INFORMATION: Synthetic

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Phe Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Pro Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Arg Leu Glu Ile Lys
            100                 105

<210> SEQ ID NO 77
<211> LENGTH: 107
<212> TYPE: PRT
<213> ORGANISM: Artificial Sequence
<220> FEATURE:
<223> OTHER INFORMATION: Synthetic

<400> SEQUENCE: 77
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Phe Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Arg Leu Glu Ile Lys
            100                 105

<210> SEQ ID NO 78
<211> LENGTH: 107
<212> TYPE: PRT
<213> ORGANISM: Artificial Sequence
<220> FEATURE:
<223> OTHER INFORMATION: Synthetic

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Phe Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Asn Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Gln Tyr Ser Thr Pro Trp
                85                  90                  95

Thr Phe Gly Gln Gly Thr Arg Leu Glu Ile Lys
            100                 105

<210> SEQ ID NO 79
<211> LENGTH: 107
<212> TYPE: PRT
<213> ORGANISM: Artificial Sequence
<220> FEATURE:
<223> OTHER INFORMATION: Synthetic

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Phe Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Met Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

```
<210> SEQ ID NO 80
<211> LENGTH: 107
<212> TYPE: PRT
<213> ORGANISM: Artificial Sequence
<220> FEATURE:
<223> OTHER INFORMATION: Synthetic

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Phe Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Asp Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Arg Leu Glu Ile Lys
            100                 105
```

Before the SEQ ID NO 80 block, the preceding sequence ends with:

```
Thr Phe Gly Gln Gly Thr Arg Leu Glu Ile Lys
            100                 105
```